US012669495B2

(12) United States Patent
Fukuyama et al.

(10) Patent No.: US 12,669,495 B2
(45) Date of Patent: Jun. 30, 2026

(54) AUTOMATIC ANALYSIS DEVICE AND AUTOMATIC ANALYSIS METHOD

(71) Applicant: Hitachi High-Tech Corporation, Tokyo (JP)

(72) Inventors: Michiko Fukuyama, Tokyo (JP); Chie Yabutani, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 135 days.

(21) Appl. No.: 18/835,747

(22) PCT Filed: Oct. 6, 2022

(86) PCT No.: PCT/JP2022/037502
§ 371 (c)(1),
(2) Date: Aug. 5, 2024

(87) PCT Pub. No.: WO2023/171013
PCT Pub. Date: Sep. 14, 2023

(65) Prior Publication Data
US 2025/0137993 A1 May 1, 2025

(30) Foreign Application Priority Data

Mar. 9, 2022 (JP) ................................. 2022-036099

(51) Int. Cl.
*G01N 33/49* (2006.01)
*G01N 21/25* (2006.01)
(Continued)

(52) U.S. Cl.
CPC ....... *G01N 33/4905* (2013.01); *G01N 21/253* (2013.01); *G01N 21/272* (2013.01);
(Continued)

(58) Field of Classification Search
CPC ............. G01N 33/4905; G01N 21/253; G01N 21/272; G01N 35/00584; G01N 35/1002; G01N 2035/0097
See application file for complete search history.

(56) References Cited

U.S. PATENT DOCUMENTS 6,524,861 B1    2/2003  Anderson
2018/0080948 A1*  3/2018  Yabutani ................ G01N 21/82
(Continued)

FOREIGN PATENT DOCUMENTS

JP        2003-57248 A    2/2003
JP        2005-61887 A    3/2005
(Continued)

OTHER PUBLICATIONS

International Search Report of PCT/JP2022/037502 dated Dec. 13, 2022.
Extended European Search Report received in corresponding European Application No. 22930990.1 dated Jan. 29, 2026.

*Primary Examiner* — Jamil Ahmed
(74) *Attorney, Agent, or Firm* — MATTINGLY & MALUR, PC

(57) ABSTRACT

An automatic analysis device includes: a specimen dispenser mechanism; a reagent dispenser mechanism; a measuring unit; an analysis operation control unit that controls the operation of the specimen dispenser mechanism, the reagent dispenser mechanism and the measuring unit; a coagulation time arithmetic unit that calculates a coagulation time on the basis of light intensity measured at the measuring unit; a graph generating unit that generates a graph pertaining to the coagulation time of each preparation specimen calculated at the coagulation time arithmetic unit; and a display unit that displays the graph generated by the graph generating unit, wherein if a preparation specimen exists for which a coagulation time cannot be calculated, the graph generating unit generates a graph using at least either a coagulation time
(Continued)

calculated for a preparation specimen prepared outside the automatic analysis device, or an estimated coagulation time on the basis of the light intensity measured.

17 Claims, 17 Drawing Sheets

(51) Int. Cl.
  *G01N 21/27*     (2006.01)
  *G01N 35/00*     (2006.01)
  *G01N 35/10*     (2006.01)
(52) U.S. Cl.
  CPC .................. *G01N 35/00584* (2013.01); *G01N 35/1002* (2013.01); *G01N 2035/0097* (2013.01)

(56)                    References Cited

U.S. PATENT DOCUMENTS

| | | |
|---|---|---|
| 2020/0103420 A1 | 4/2020 | Kurono et al. |
| 2022/0373565 A1 | 11/2022 | Kawabe et al. |
| 2024/0027476 A1 | 1/2024 | Kawabe et al. |

FOREIGN PATENT DOCUMENTS

| | | |
|---|---|---|
| JP | 2006-17600 A | 1/2006 |
| JP | 2019-215357 A | 12/2019 |
| JP | 2020-56622 A | 4/2020 |
| WO | 2016/002394 A1 | 1/2016 |
| WO | 2016/152305 A1 | 9/2016 |
| WO | 2020/256107 A1 | 12/2020 |
| WO | 2022/054819 A1 | 9/2021 |

* cited by examiner

[FIG. 1]
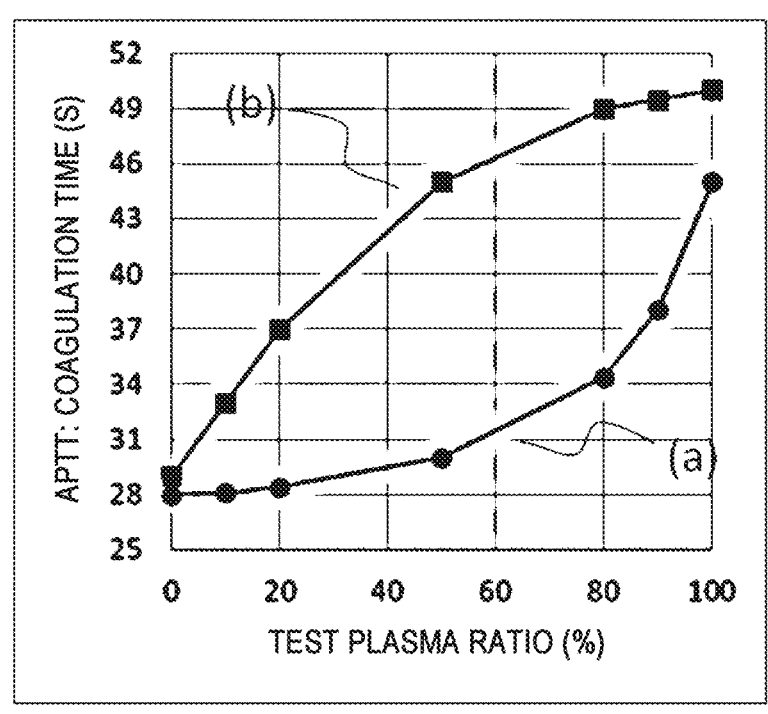

[FIG. 2]
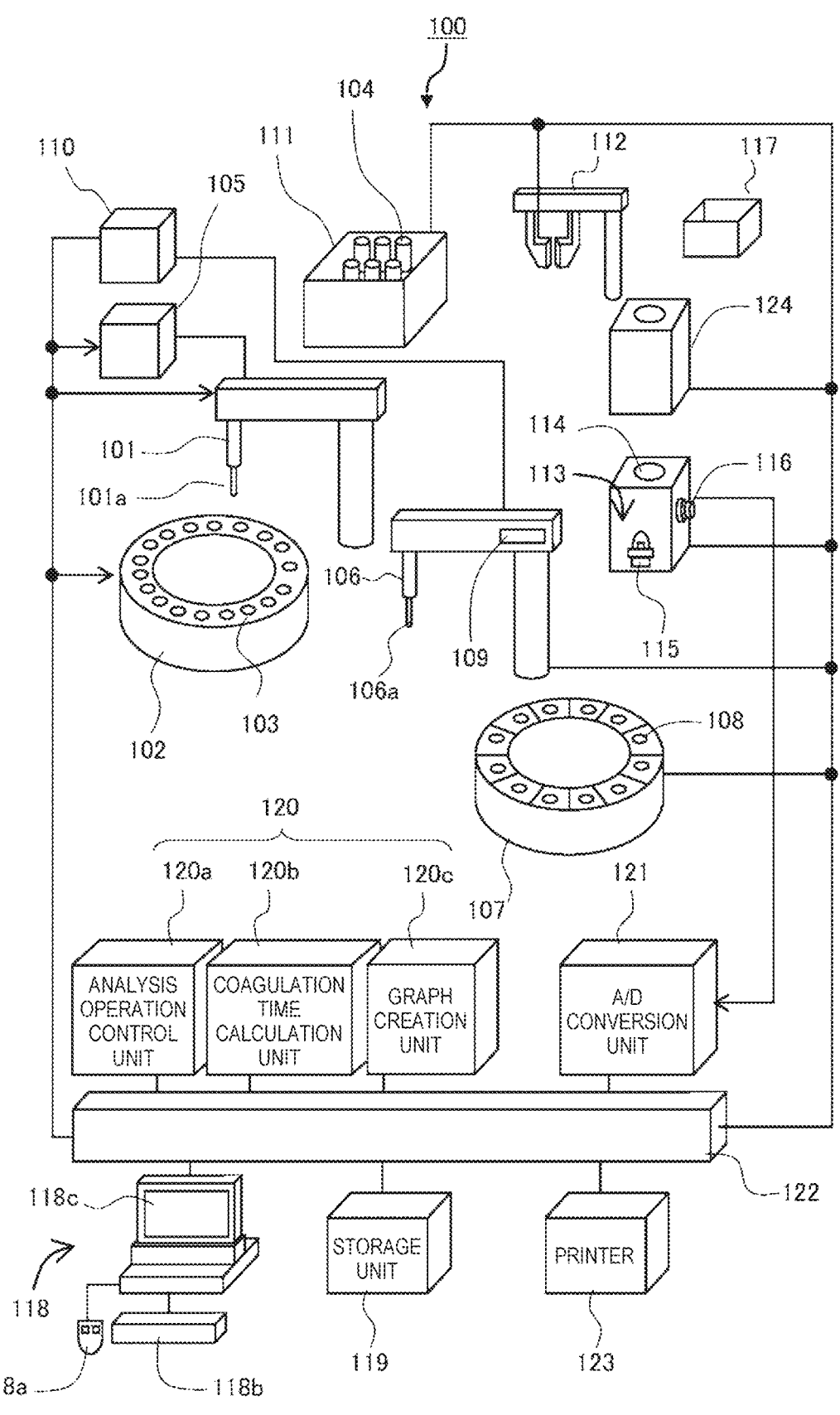

[FIG. 3]
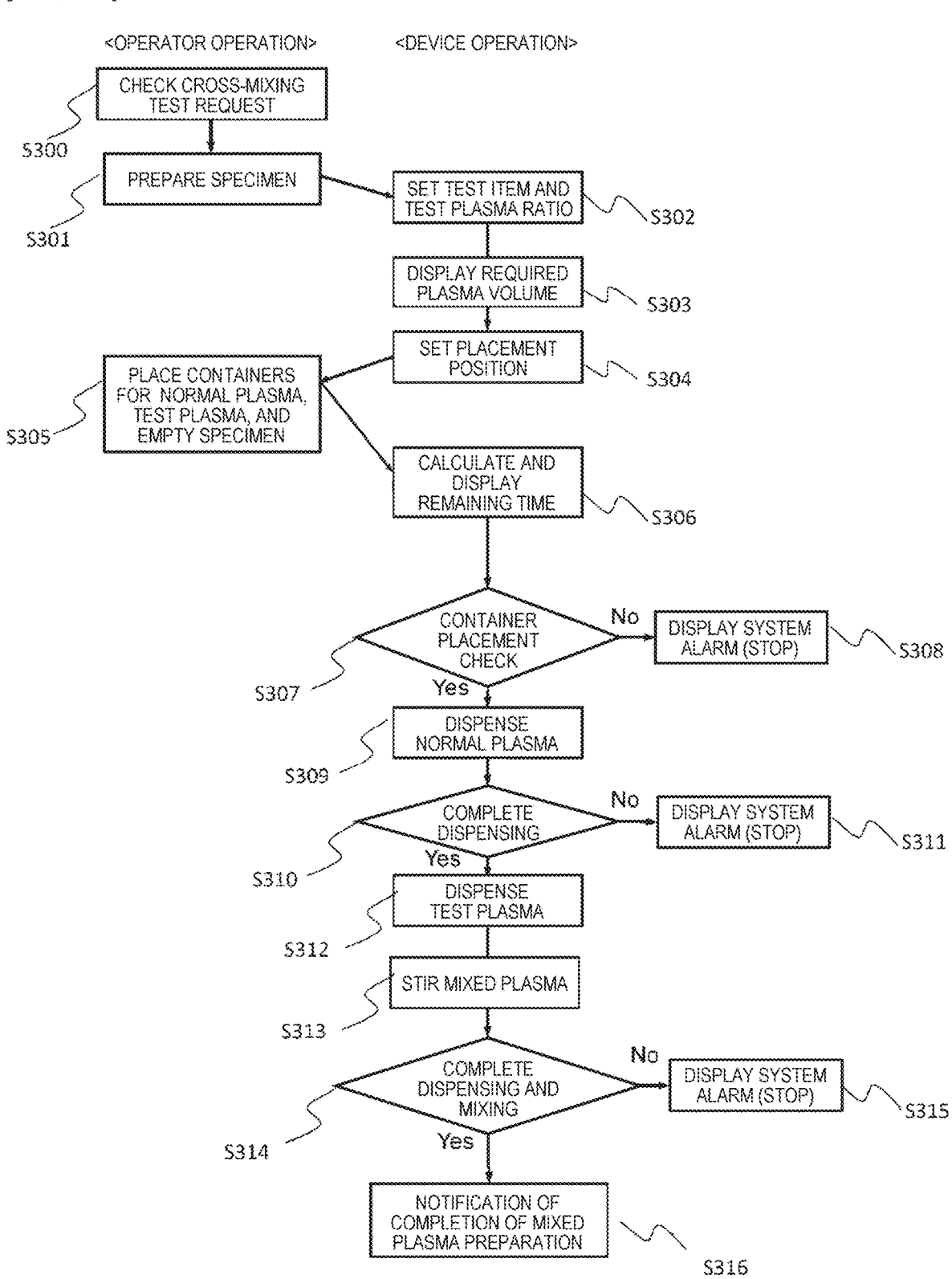

[FIG. 4]

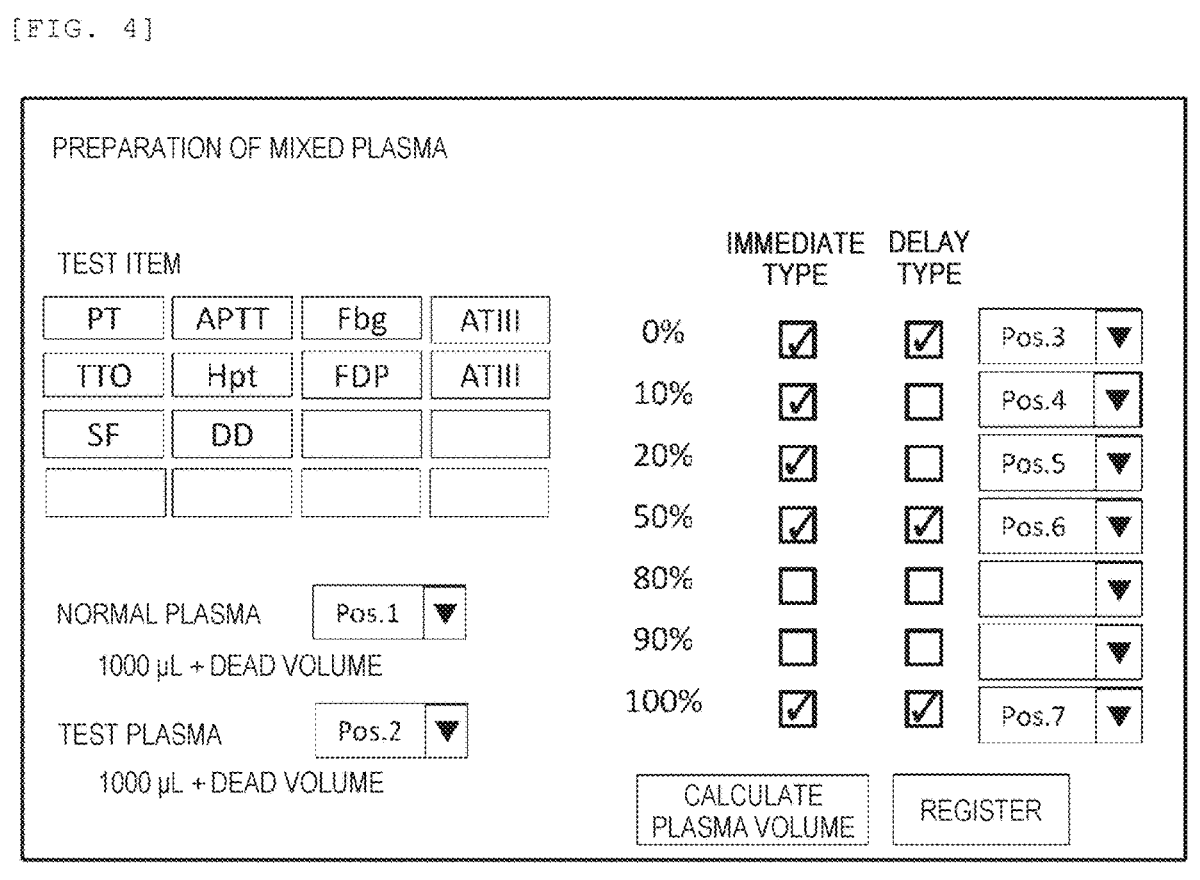

PREPARATION OF MIXED PLASMA

TEST ITEM

| PT | APTT | Fbg | ATIII |
| TTO | Hpt | FDP | ATIII |
| SF | DD | | |
| | | | |

|  | IMMEDIATE TYPE | DELAY TYPE | |
| --- | --- | --- | --- |
| 0% | ☑ | ☑ | Pos.3 ▼ |
| 10% | ☑ | ☐ | Pos.4 ▼ |
| 20% | ☑ | ☐ | Pos.5 ▼ |
| 50% | ☑ | ☑ | Pos.6 ▼ |
| 80% | ☐ | ☐ | ▼ |
| 90% | ☐ | ☐ | ▼ |
| 100% | ☑ | ☑ | Pos.7 ▼ |

NORMAL PLASMA    Pos.1 ▼
1000 µL + DEAD VOLUME

TEST PLASMA    Pos.2 ▼
1000 µL + DEAD VOLUME

CALCULATE PLASMA VOLUME          REGISTER

[FIG. 5]
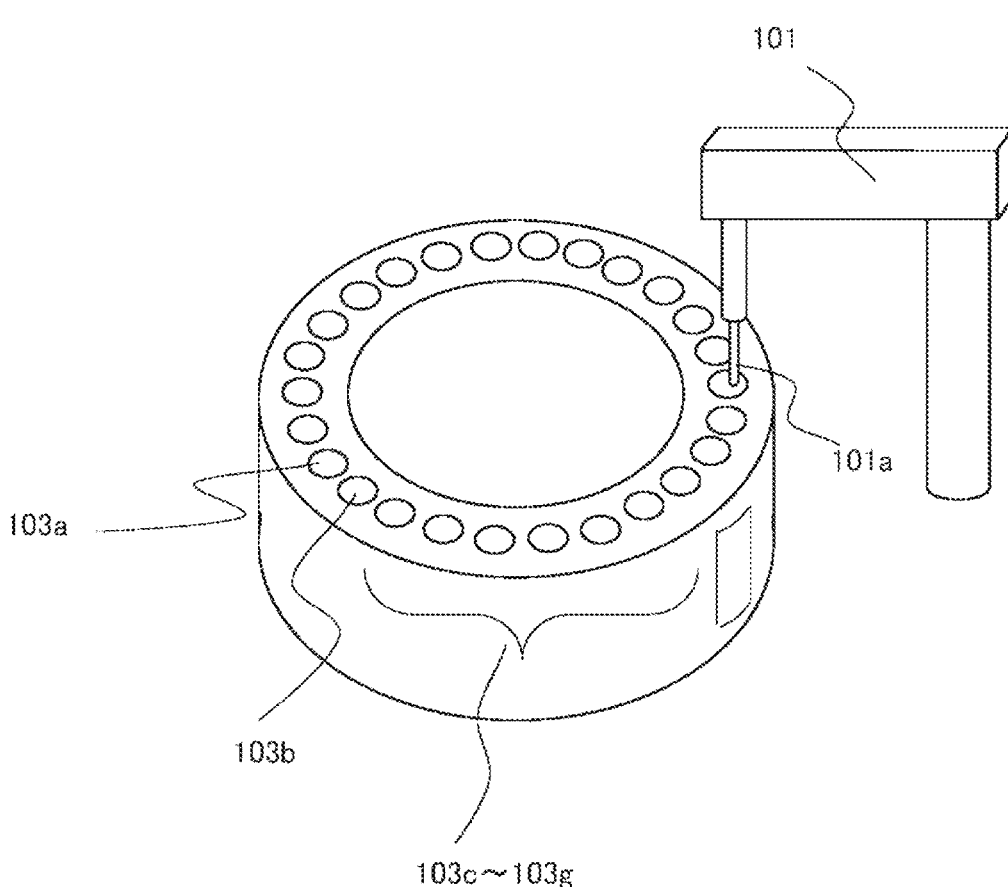

[FIG. 6]
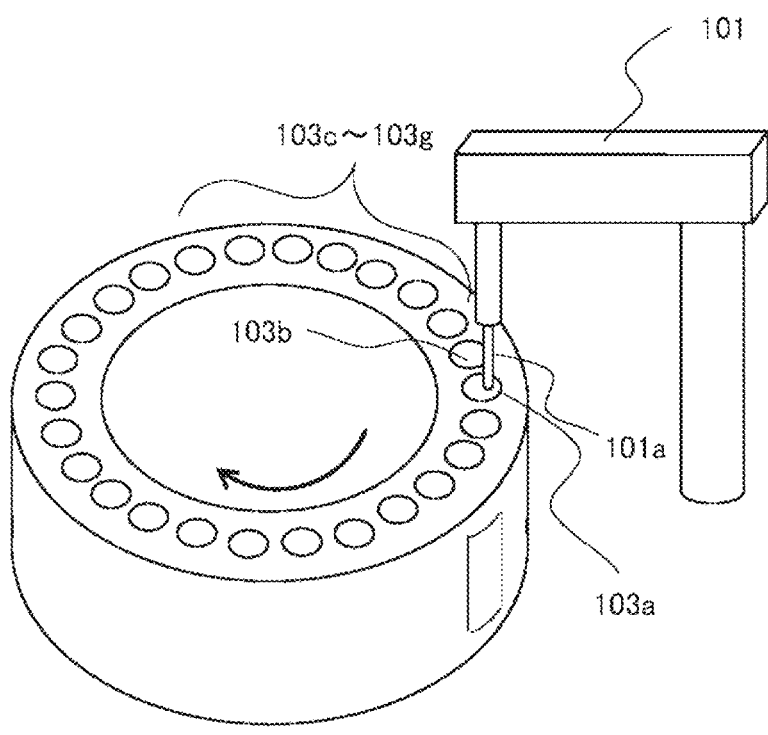
[FIG. 7]
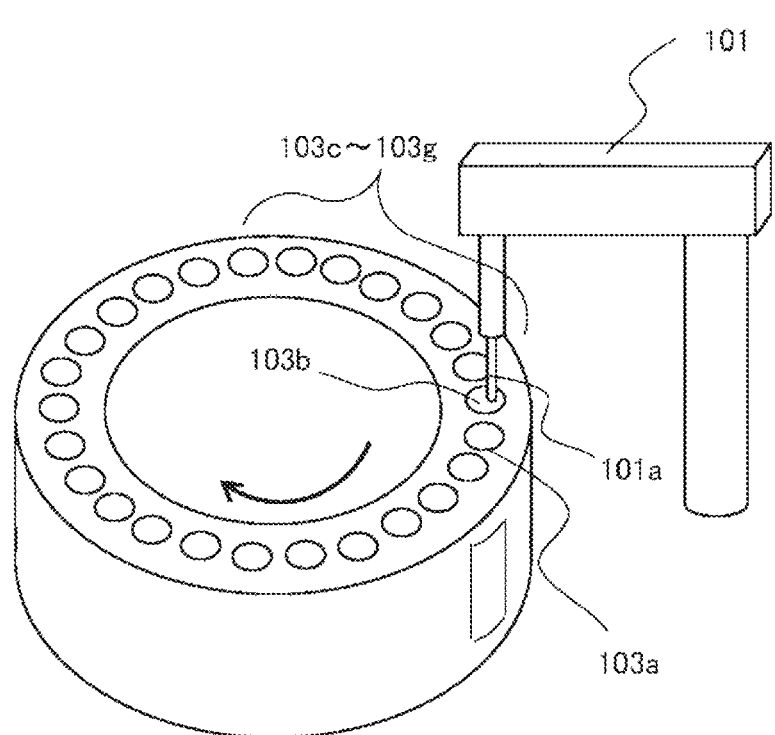

[FIG. 8]
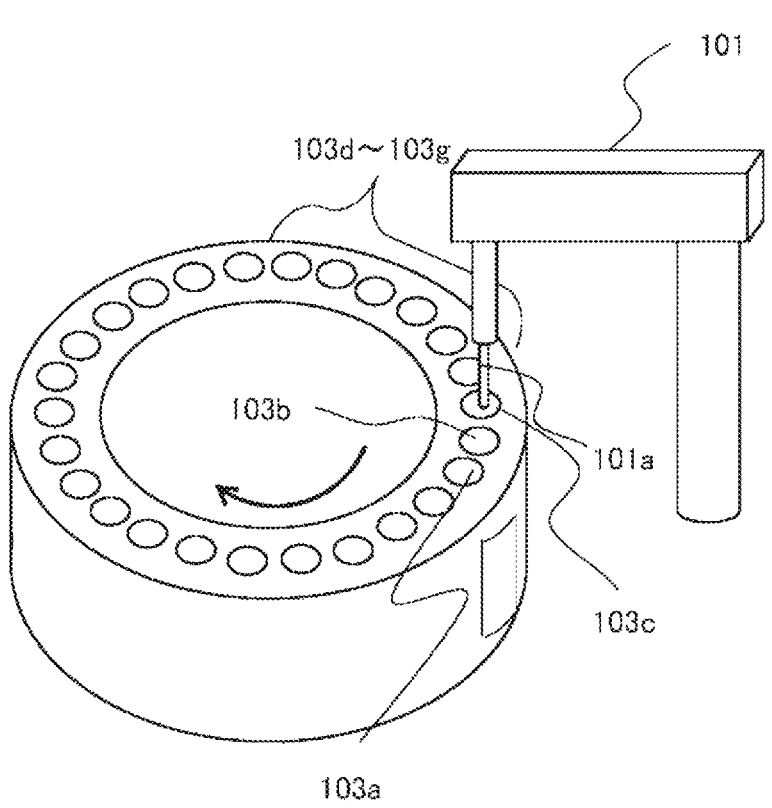

[FIG. 9]
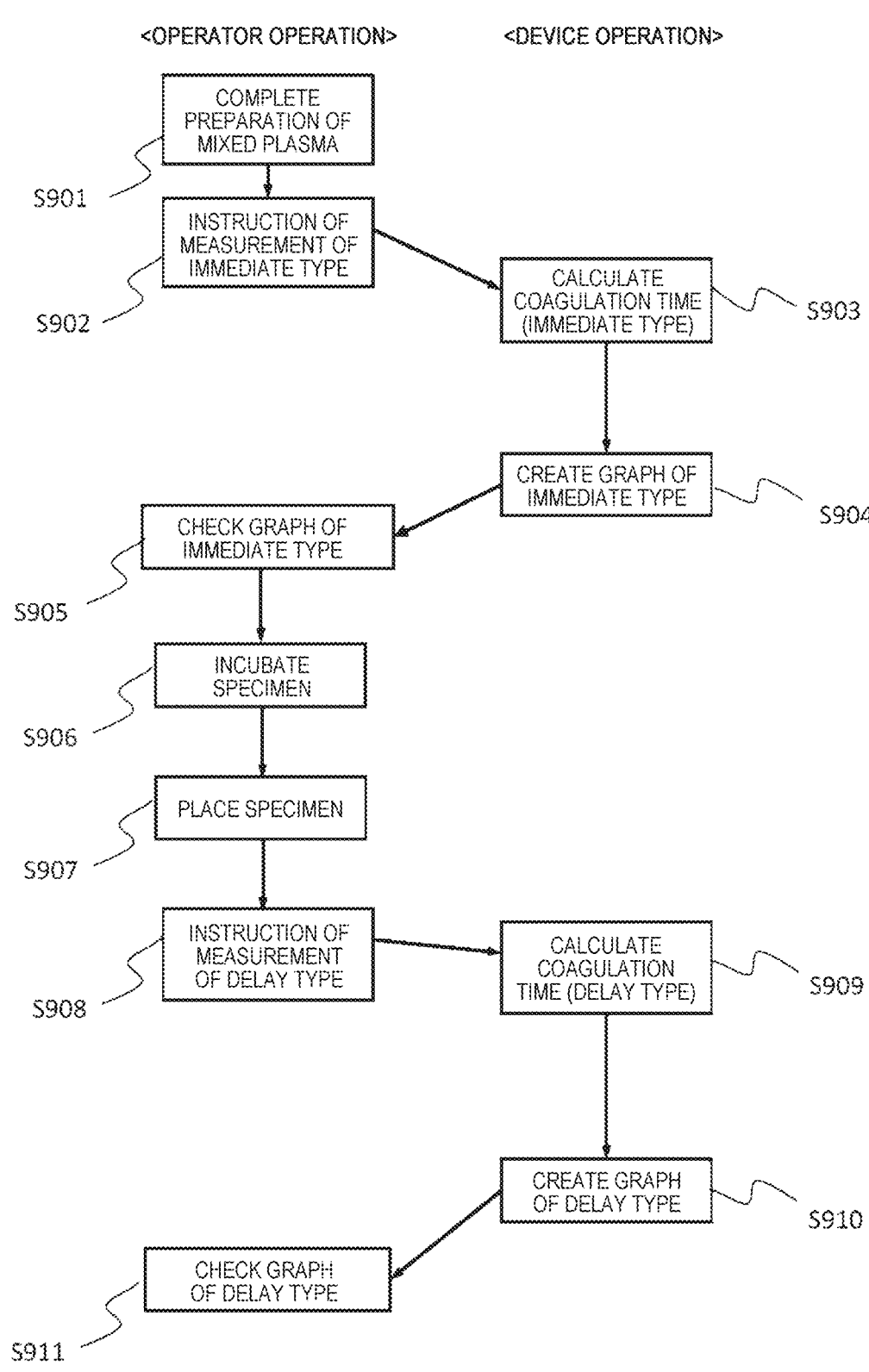

[FIG. 10]
PREPARATION OF MIXED PLASMA
COMPLETE PREPARATION
OF MIXED PLASMA
IS IMMEDIATE TYPE MEASURED AS IT IS?
| Pos. | TEST PLASMA RATIO | ITEM |
|------|-------------------|------|
| 3 | 0% | APTT |
| 4 | 10% | APTT |
| 5 | 20% | APTT |
| 6 | 50% | APTT |
| 7 | 100% | APTT |
| YES | NO |
[FIG. 11]
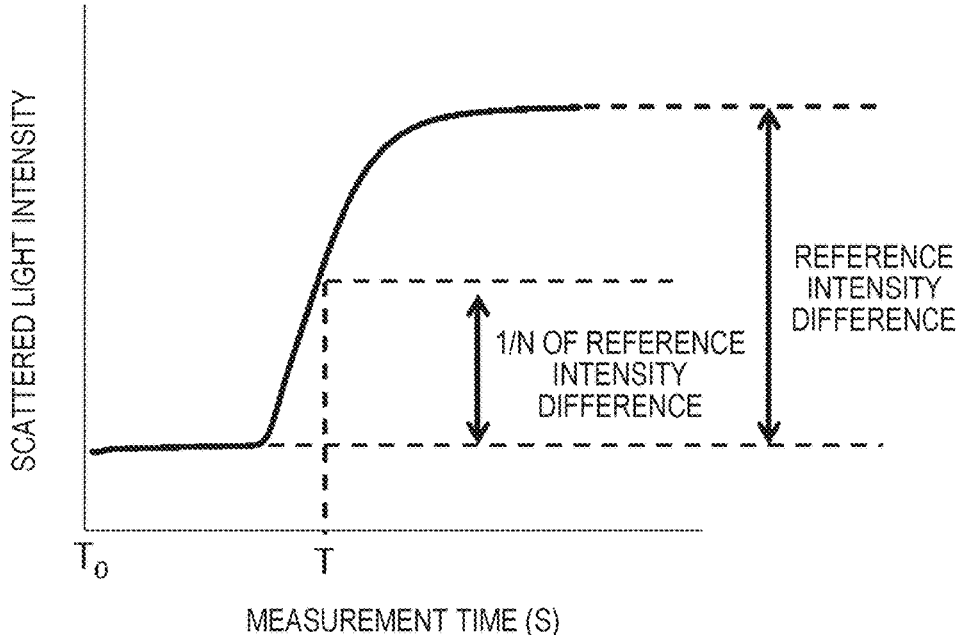

[FIG. 12]
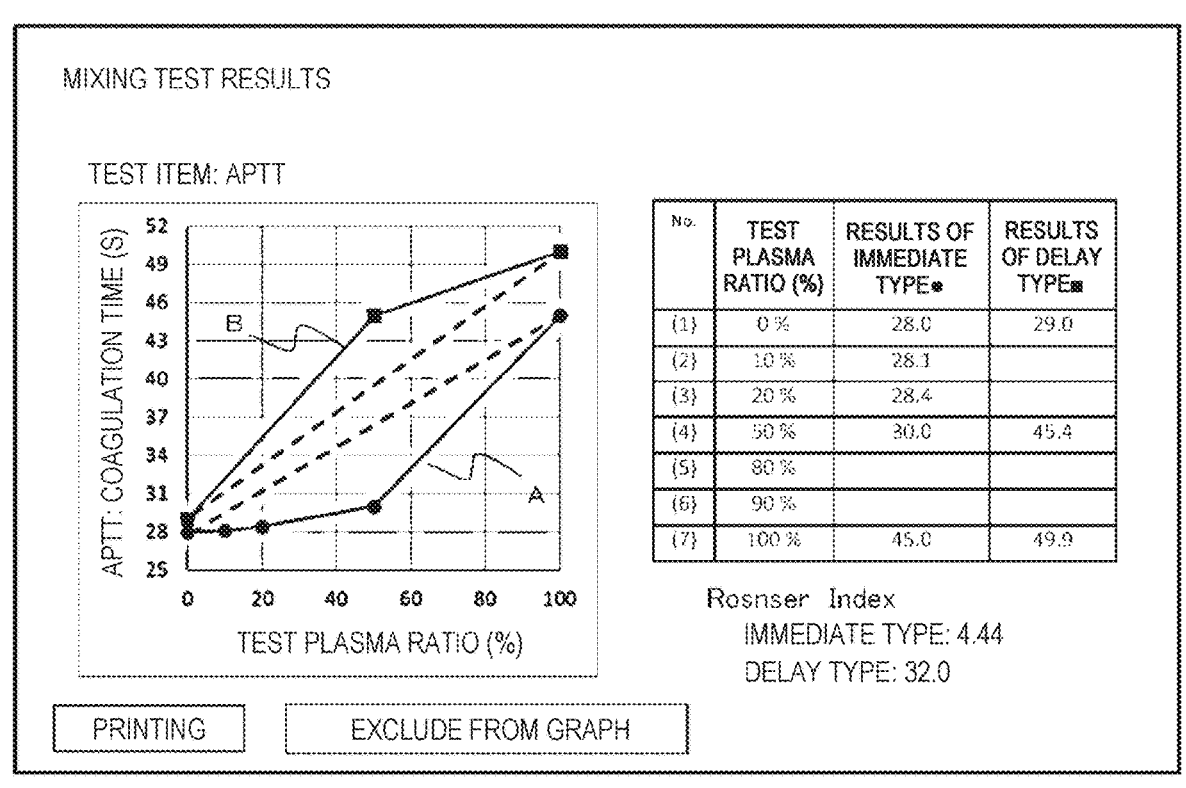
MIXING TEST RESULTS
TEST ITEM: APTT
| No. | TEST PLASMA RATIO (%) | RESULTS OF IMMEDIATE TYPE● | RESULTS OF DELAY TYPE■ |
|---|---|---|---|
| (1) | 0 % | 28.0 | 29.0 |
| (2) | 10 % | 28.1 | |
| (3) | 20 % | 28.4 | |
| (4) | 50 % | 30.0 | 45.4 |
| (5) | 80 % | | |
| (6) | 90 % | | |
| (7) | 100 % | 45.0 | 49.9 |
Rosner Index
  IMMEDIATE TYPE: 4.44
  DELAY TYPE: 32.0
PRINTING          EXCLUDE FROM GRAPH

[FIG. 13]

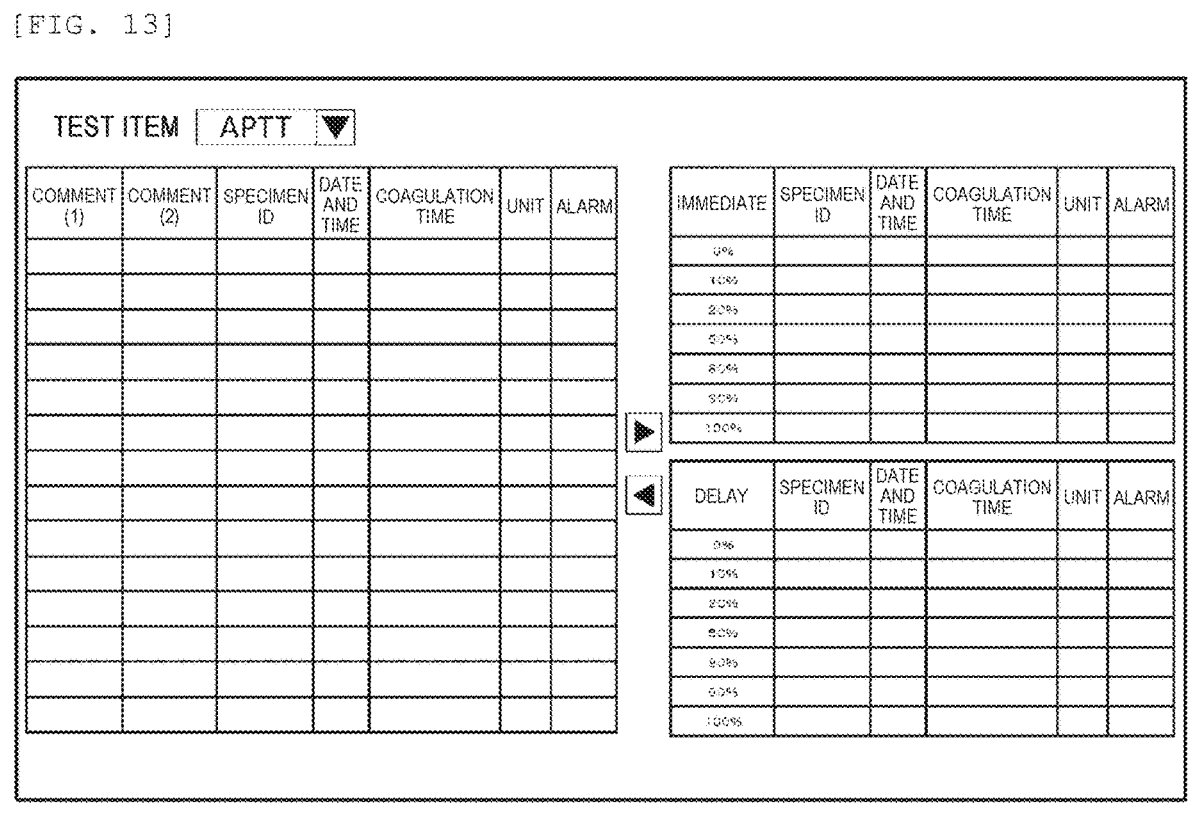

TEST ITEM [ APTT ▼ ]

| COMMENT (1) | COMMENT (2) | SPECIMEN ID | DATE AND TIME | COAGULATION TIME | UNIT | ALARM |
|---|---|---|---|---|---|---|
| | | | | | | |
| | | | | | | |
| | | | | | | |
| | | | | | | |
| | | | | | | |
| | | | | | | |
| | | | | | | |
| | | | | | | |
| | | | | | | |
| | | | | | | |
| | | | | | | |
| | | | | | | |
| | | | | | | |
| | | | | | | |

▶

| IMMEDIATE | SPECIMEN ID | DATE AND TIME | COAGULATION TIME | UNIT | ALARM |
|---|---|---|---|---|---|
| 0% | | | | | |
| 10% | | | | | |
| 20% | | | | | |
| 50% | | | | | |
| 80% | | | | | |
| 90% | | | | | |
| 100% | | | | | |

◀

| DELAY | SPECIMEN ID | DATE AND TIME | COAGULATION TIME | UNIT | ALARM |
|---|---|---|---|---|---|
| 0% | | | | | |
| 10% | | | | | |
| 20% | | | | | |
| 80% | | | | | |
| 90% | | | | | |
| 90% | | | | | |
| 100% | | | | | |

[FIG. 14]
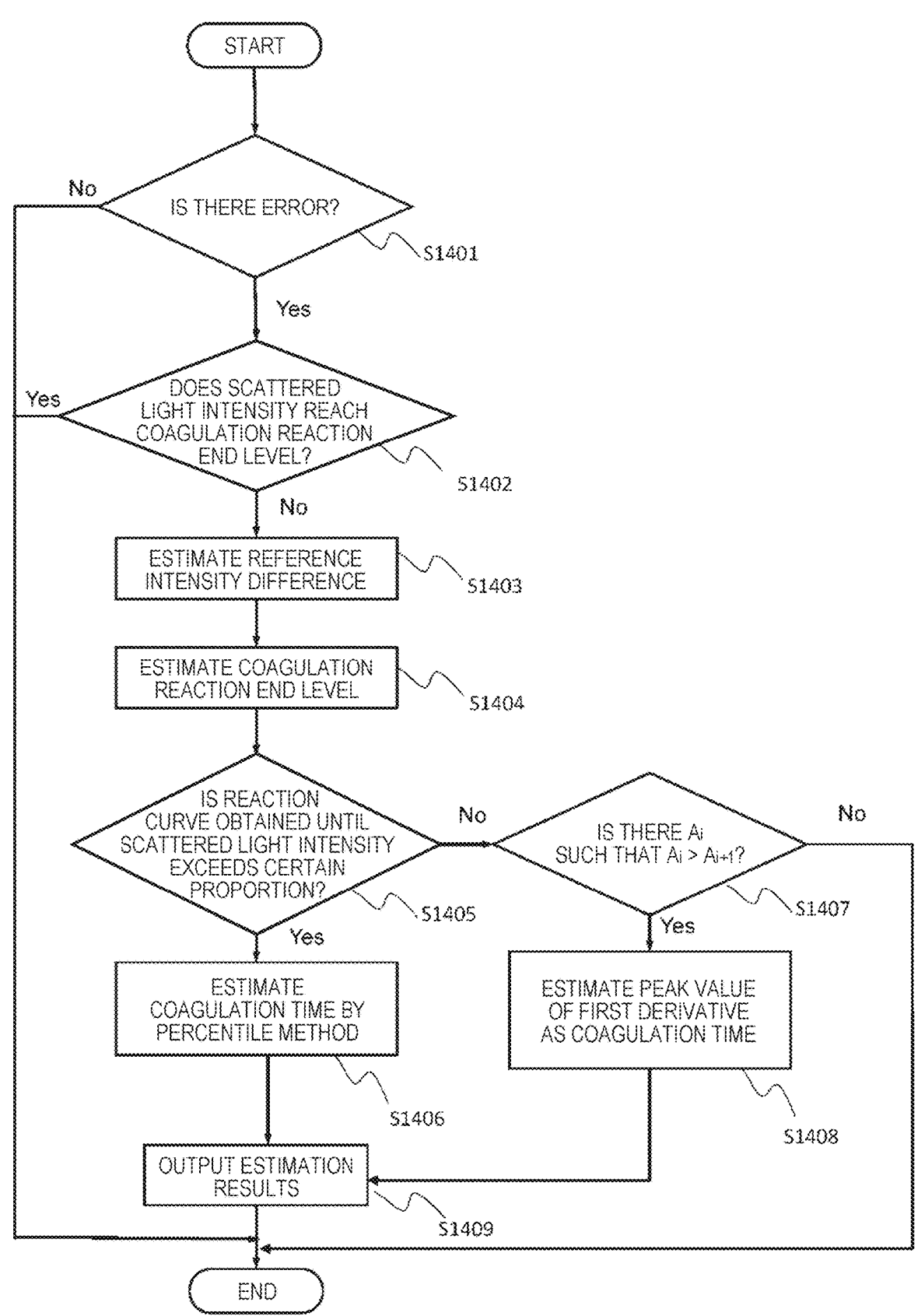

[FIG. 15]
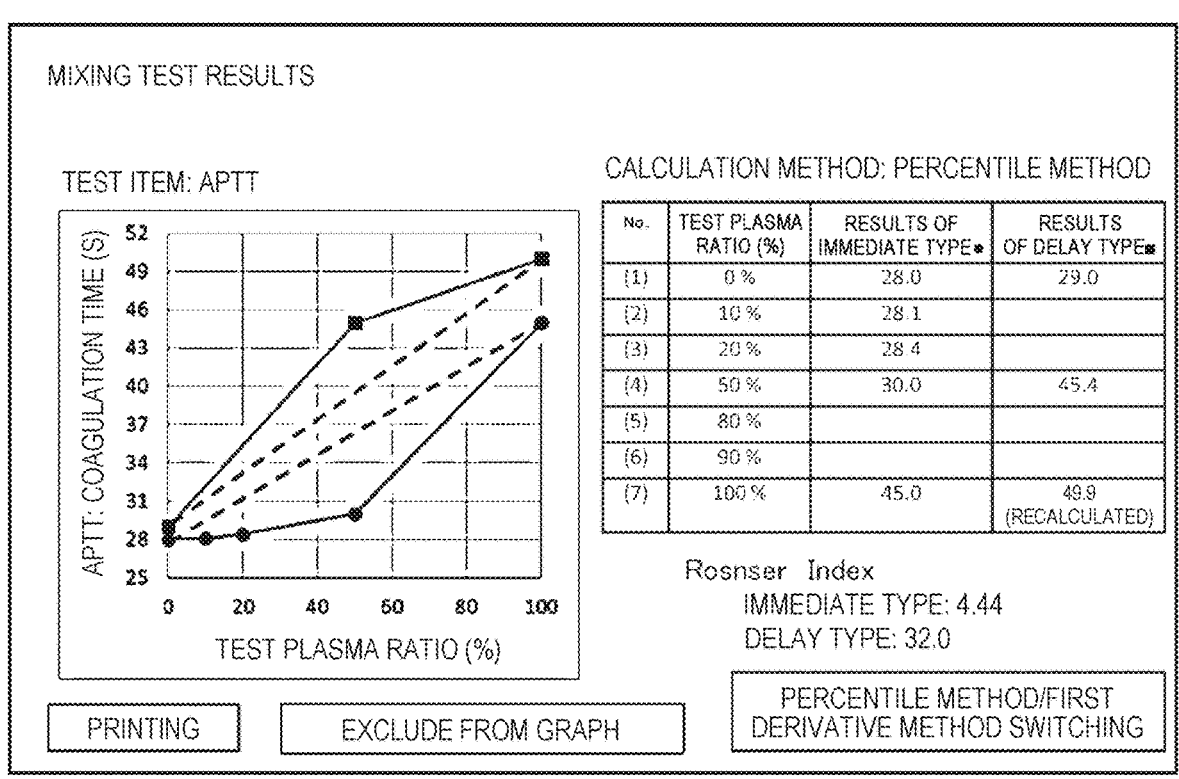
[FIG. 16]
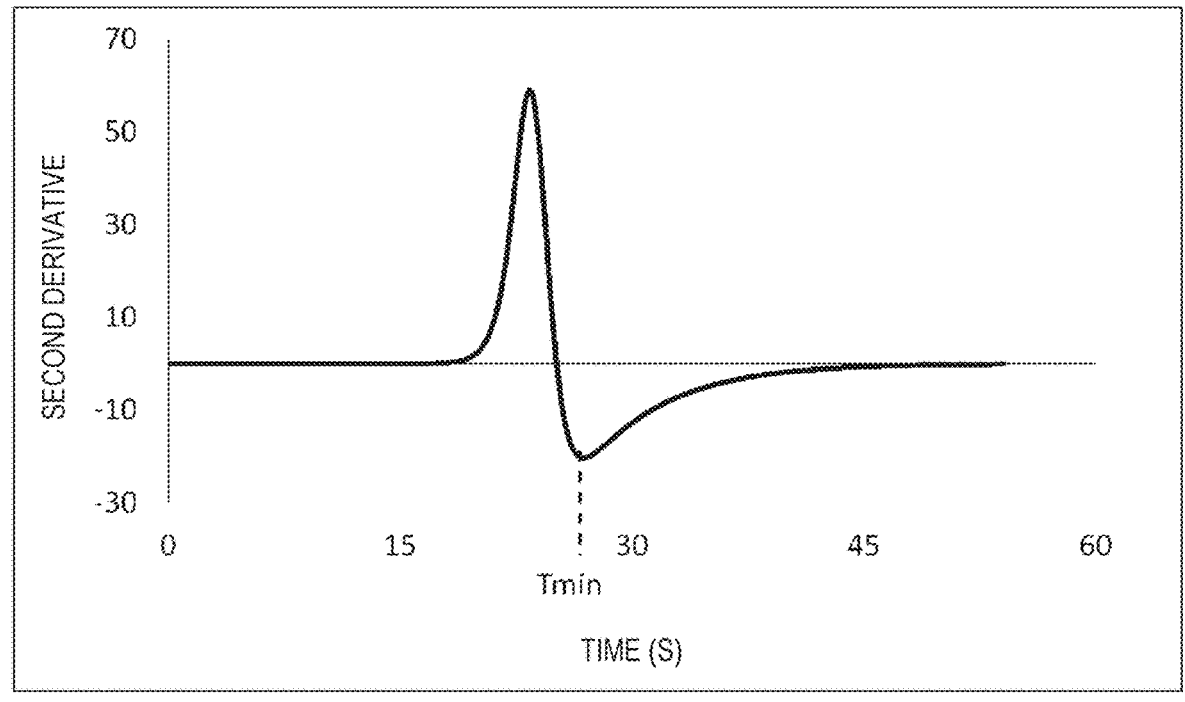

[FIG. 17]
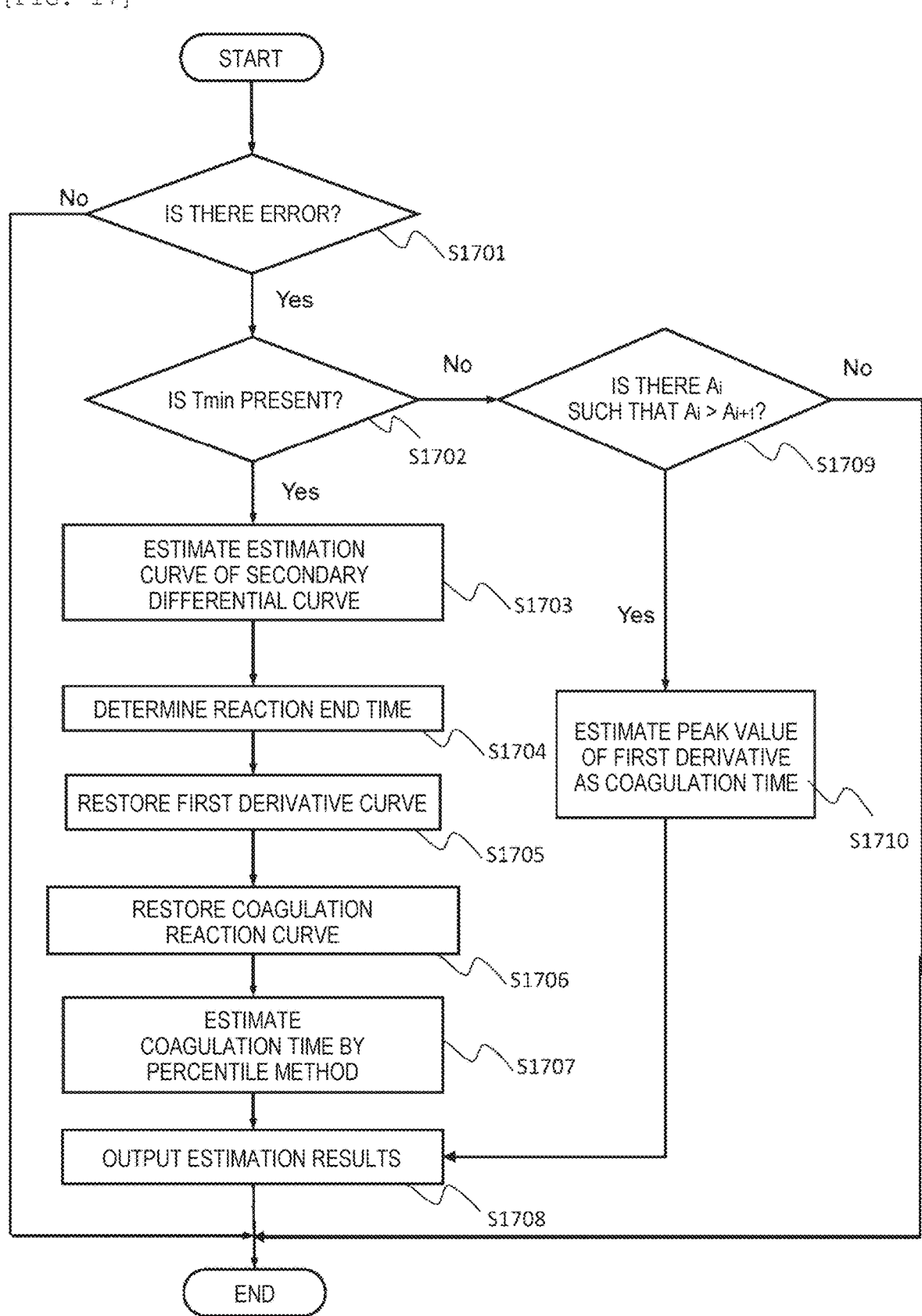

[FIG. 18]

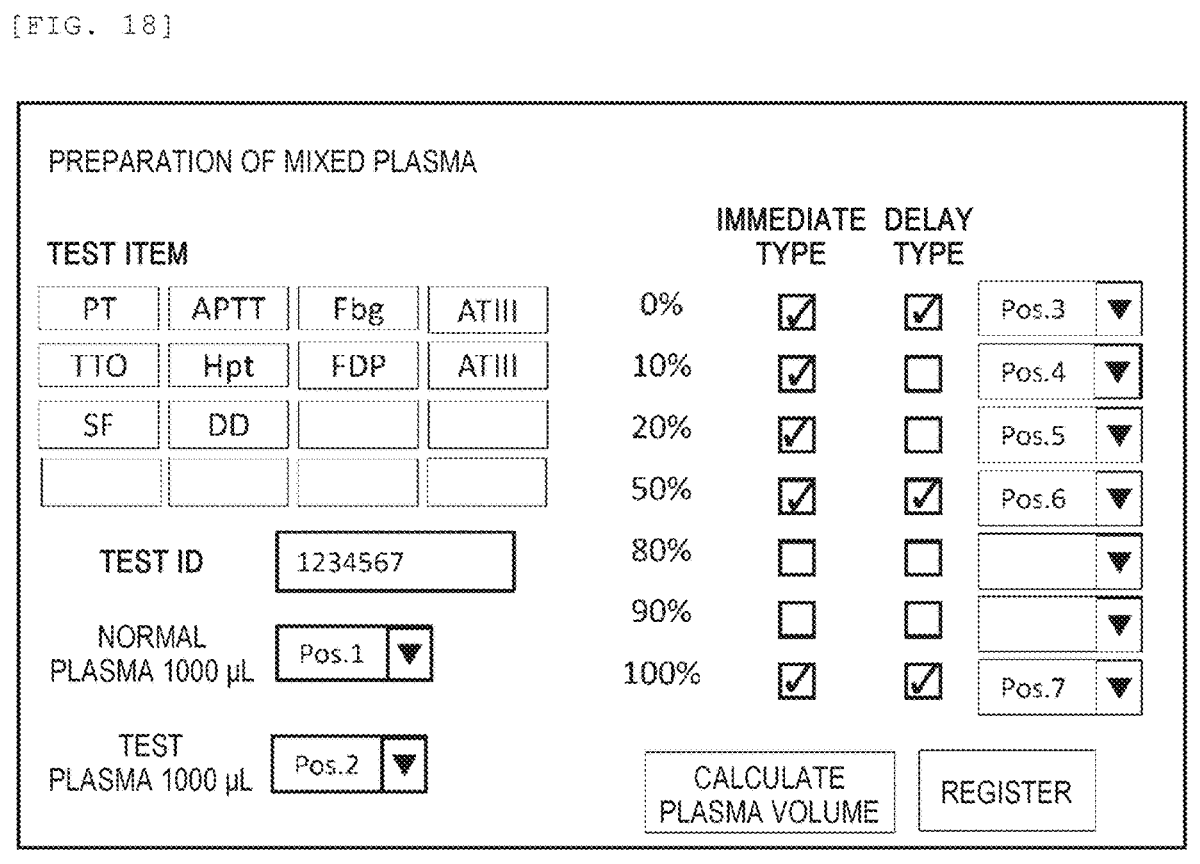

PREPARATION OF MIXED PLASMA

| TEST ITEM | | | | | IMMEDIATE TYPE | DELAY TYPE | |
|---|---|---|---|---|---|---|---|
| PT | APTT | Fbg | ATIII | 0% | ☑ | ☑ | Pos.3 ▼ |
| TTO | Hpt | FDP | ATIII | 10% | ☑ | ☐ | Pos.4 ▼ |
| SF | DD | | | 20% | ☑ | ☐ | Pos.5 ▼ |
| | | | | 50% | ☑ | ☑ | Pos.6 ▼ |

TEST ID      1234567

NORMAL PLASMA 1000 µL    Pos.1 ▼

TEST PLASMA 1000 µL    Pos.2 ▼

80%   ☐   ☐

90%   ☐   ☐       ▼

100%   ☑   ☑   Pos.7 ▼

CALCULATE PLASMA VOLUME      REGISTER

[FIG. 19]
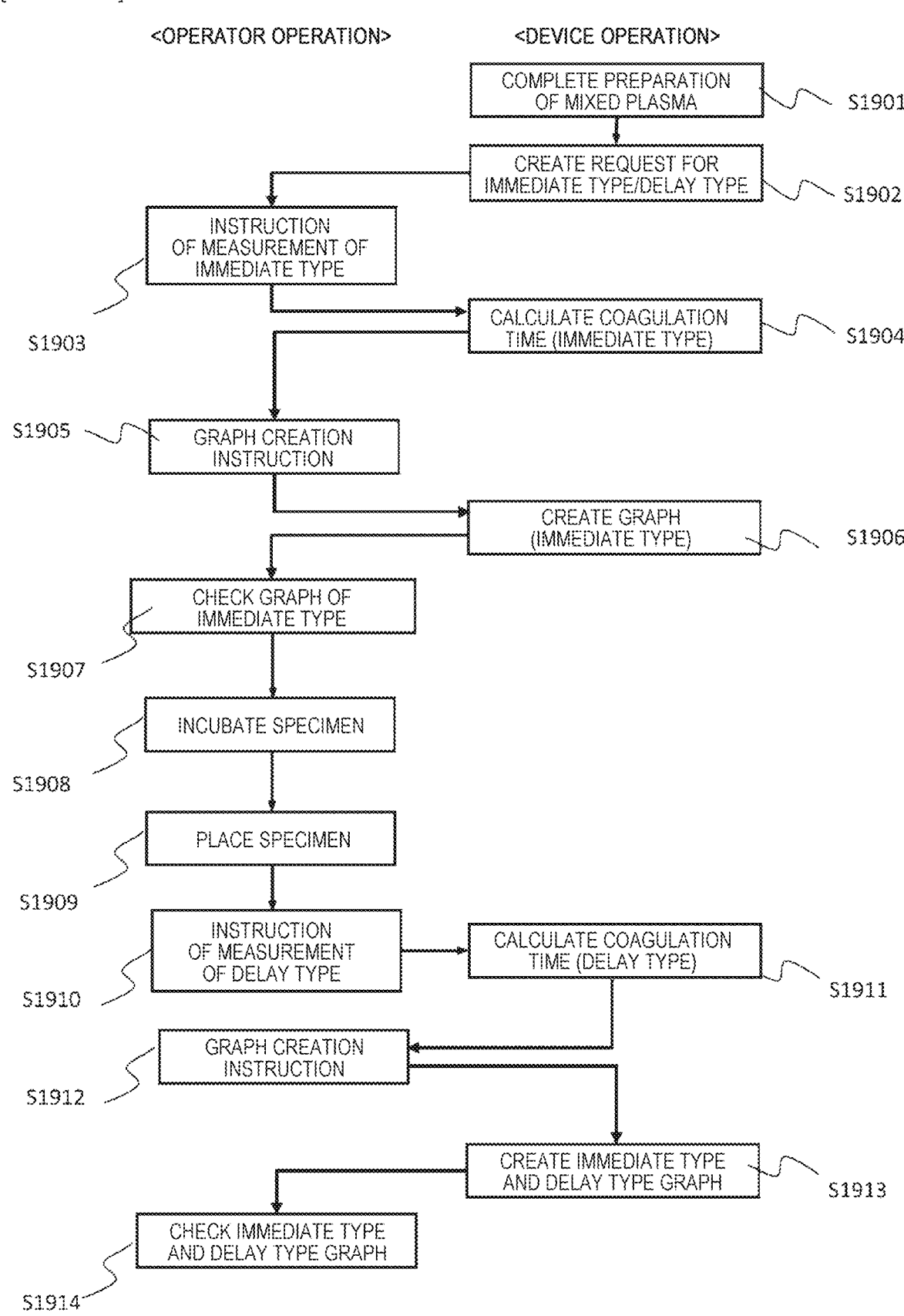

[FIG. 20]

| COMMENT (1) | COMMENT (2) | SPECIMEN ID | DATE AND TIME | COAGULATION TIME | UNIT | ALARM |
|---|---|---|---|---|---|---|
| | | | | | | |
| | | | | | | |
| | | | | | | |
| | | | | | | |
| | | | | | | |
| | | | | | | |
| | | | | | | |
| | | | | | | |
| | | | | | | |
| | | | | | | |
| | | | | | | |
| | | | | | | |
| | | | | | | |

TEST ID    1234567 ▼

| IMMEDIATE | SPECIMEN ID | DATE AND TIME | COAGULATION TIME | UNIT | ALARM |
|---|---|---|---|---|---|
| 0% | | | | | |
| 10% | | | | | |
| 20% | | | | | |
| 50% | | | | | |
| 80% | | | | | |
| 90% | | | | | |
| 100% | | | | | |

| DELAY | SPECIMEN ID | DATE AND TIME | COAGULATION TIME | UNIT | ALARM |
|---|---|---|---|---|---|
| 0% | | | | | |
| 10% | | | | | |
| 20% | | | | | |
| 50% | | | | | |
| 80% | | | | | |
| 90% | | | | | |
| 100% | | | | | |

CREATE GRAPH

[FIG. 21]

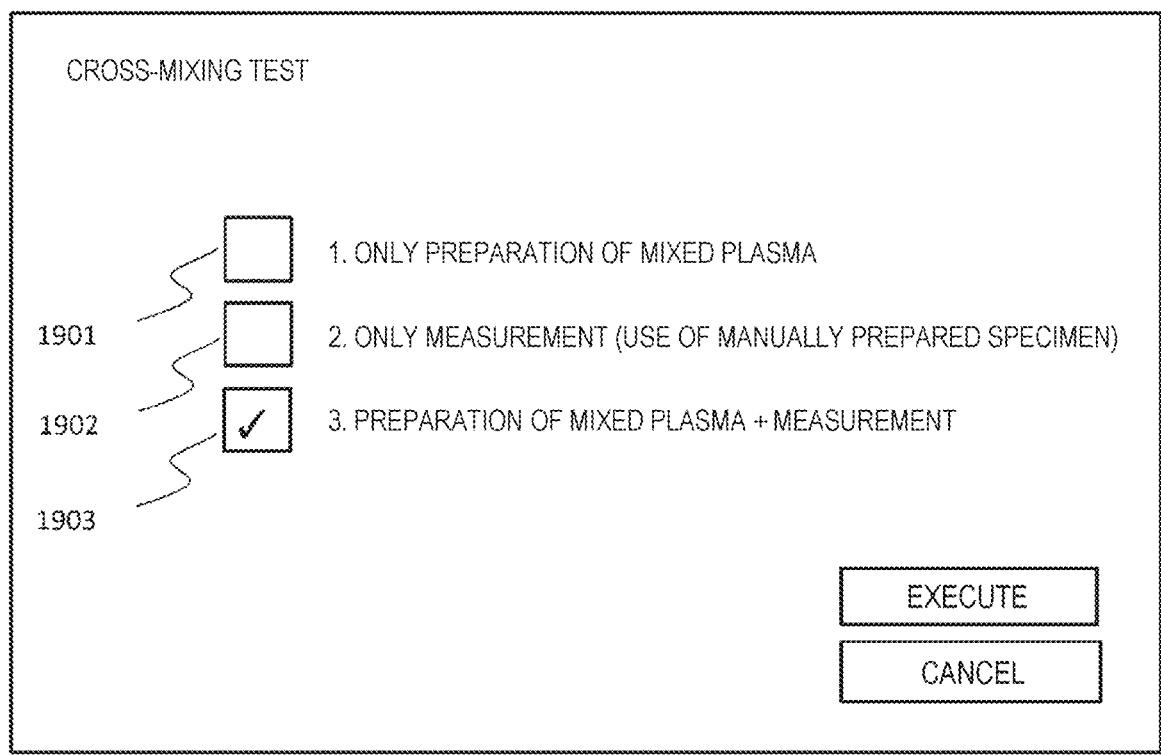

CROSS-MIXING TEST

1901

1902

1903

☐  1. ONLY PREPARATION OF MIXED PLASMA

☐  2. ONLY MEASUREMENT (USE OF MANUALLY PREPARED SPECIMEN)

☑  3. PREPARATION OF MIXED PLASMA + MEASUREMENT

EXECUTE

CANCEL

AUTOMATIC ANALYSIS DEVICE AND AUTOMATIC ANALYSIS METHOD

TECHNICAL FIELD

The present invention relates to an automatic analysis device and an automatic analysis method.

BACKGROUND ART

A blood coagulation test is performed for the purpose of grasping a pathological condition of a blood coagulation-fibrinolysis system, diagnosing disseminated intravascular coagulation (DIC), checking a thrombosis treatment effect, and diagnosing hemophilia. In particular, a blood coagulation time measurement is to measure a time until a fibrin clot forms after mixing a specimen with a reagent. In the cases of congenital or acquired abnormalities, the coagulation time is prolonged. The cause of the prolongation of the coagulation time may be an activity reduction (deficient type) due to deficiency of a coagulation factor, and an activity reduction (inhibitor type) due to inhibition of a coagulation reaction of an antibody to components constituting the coagulation system or components in a coagulation time measurement reagent. Therefore, a cross-mixing test is known as a method for determining whether the cause of the prolongation of the coagulation time is a deficient type or an inhibitor type. The cross-mixing test is to determine, in a graph form, the degree of correction of the coagulation time of a prepared specimen obtained by adding normal plasma to test plasma. For example, PTL 1 discloses an automatic analysis device that automates preparation of mixed plasma obtained by mixing test plasma and normal plasma at a predetermined mixing ratio.

CITATION LIST

Patent Literature

PTL 1: WO16/152305

SUMMARY OF INVENTION

Technical Problem

However, in the cross-mixing test, for example, when a coagulation time of a prepared specimen containing only the test plasma is prolonged and a coagulation reaction is not completed within the predetermined time, the coagulation time cannot be calculated. When only one prepared specimen for which a coagulation time cannot be calculated is present, a graph is not output, and it may be difficult to determine whether the cause of the prolongation of the coagulation time is a deficient type or an inhibitor type.

An object of the invention is to provide an automatic analysis device and an automatic analysis method capable of performing a determination by using a cross-mixing test even when there is a prepared specimen for which a coagulation time cannot be calculated.

Solution to Problem

In order to solve the above problems, an automatic analysis device according to the invention includes: a specimen dispensing mechanism; a reagent dispensing mechanism; a measurement unit; an analysis operation control unit configured to control operations of the specimen dispensing mechanism, the reagent dispensing mechanism, and the measurement unit; a coagulation time calculation unit configured to calculate a coagulation time based on a light intensity measured by the measurement unit; a graph creation unit configured to create a graph related to a coagulation time of each prepared specimen calculated by the coagulation time calculation unit; and a display unit configured to display the graph created by the graph creation unit. When a prepared specimen for which the coagulation time is incalculable is present, the graph creation unit creates a graph using at least one of a coagulation time calculated by the coagulation time calculation unit for a prepared specimen prepared outside the automatic analysis device, and a coagulation time estimated by the coagulation time calculation unit based on the light intensity measured by the measurement unit.

An automatic analysis method according to the invention is an automatic analysis method using an automatic analysis device including a specimen dispensing mechanism, a reagent dispensing mechanism, a measurement unit, a coagulation time calculation unit, a graph creation unit, and a display unit. The method includes: a step of calculating, by the coagulation time calculation unit, a coagulation time based on a light intensity measured by the measurement unit; a step of creating, by the graph creation unit, a graph related to a coagulation time of each prepared specimen calculated by the coagulation time calculation unit; a step of displaying, by the display unit, the graph created by the graph creation unit; and a step of creating, by the graph creation unit, a graph using at least one of a coagulation time calculated for a prepared specimen prepared outside the automatic analysis device and a coagulation time estimated by the coagulation time calculation unit based on a light intensity measured using another prepared specimen, when a prepared specimen for which the coagulation time is incalculable is present.

Advantageous Effects of Invention

According to the invention, it is possible to provide an automatic analysis device and an automatic analysis method capable of performing a determination by using a cross-mixing test even when there is a prepared specimen for which a coagulation time cannot be calculated. As a result, not only the time required to measure a light intensity again to calculate a coagulation time can be reduced, but also re-sampling due to a shortage of plasma volume required for a re-measurement can be prevented.

Problems, configurations, and effects other than those described above will be clarified by the following description of embodiments.

BRIEF DESCRIPTION OF DRAWINGS

FIG. 1 shows an example of a graph used in a cross-mixing test.

FIG. 2 is an overall schematic configuration diagram of an automatic analysis device.

FIG. 3 is a flowchart showing a method for preparing mixed plasma used in the cross-mixing test.

FIG. 4 shows an example of a preparation setting screen of mixed plasma used in the cross-mixing test (Embodiment 1).

FIG. 5 is a diagram showing a state when a specimen dispensing mechanism checks the presence or absence of an empty specimen container.

FIG. 6 is a view showing a state in which a specimen container filled with normal plasma is at a dispensing position for the specimen dispensing mechanism.

FIG. 7 is a view showing a state in which a specimen container filled with test plasma is at a dispensing position for the specimen dispensing mechanism.

FIG. 8 is a view showing a state in which an empty specimen container is at a dispensing position for the specimen dispensing mechanism.

FIG. 9 is a flowchart showing a method for measuring a prepared specimen and creating a graph (Embodiment 1).

FIG. 10 shows an example of screens for preparation completion notification and immediate type measurement check.

FIG. 11 shows an example of a coagulation reaction curve.

FIG. 12 shows an example of a measurement result output screen (no error).

FIG. 13 shows an example of a selection screen for a measurement result used for creating a graph (Embodiment 1).

FIG. 14 is a flowchart showing a method for estimating a coagulation time by a coagulation time calculation unit according to Embodiment 1.

FIG. 15 shows an example of the measurement result output screen (with error).

FIG. 16 shows a second derivative curve of general APTT measurement results.

FIG. 17 is a flowchart showing a method for estimating a coagulation time by a coagulation time calculation unit according to Embodiment 2.

FIG. 18 shows an example of a preparation setting screen of mixed plasma used in the cross-mixing test (Embodiment 3).

FIG. 19 is a flowchart showing a method for measuring a prepared specimen and creating a graph (Embodiment 3).

FIG. 20 shows an example of a selection screen for a measurement result used for creating a graph (Embodiment 3).

FIG. 21 shows an example of a screen for selecting whether to continuously perform a measurement from the preparation of mixed plasma to the measurement.

DESCRIPTION OF EMBODIMENTS

In the present description, the term "test plasma" includes plasma from inpatients or outpatients, plasma from subjects in health checkups, and the like. The term "normal plasma" includes pooled plasma, commercially available plasma with a normal coagulation time, and the like. The pooled plasma is a pool of plasma from at least 20 apparently healthy persons. In the present description, "test plasma", "normal plasma", and "mixed plasma obtained by mixing test plasma and normal plasma (at a predetermined mixing ratio)" may be collectively referred to as a specimen for measuring a coagulation time of blood.

FIG. 1 shows an example of a graph used in a cross-mixing test. In the cross-mixing test, an activated partial thromboplastin time (APTT, may be simply referred to as the "coagulation time" hereinafter) is measured for specimens (prepared specimens) prepared by adding normal plasma to test plasma such that a proportion of the test plasma is 0%, 10%, 20%, 50%, 80%, 90%, and 100%, and the measured APTT is graphed. A horizontal axis in FIG. 1 represents a ratio (k) of the test plasma in the prepared specimen, and a vertical axis in FIG. 1 represents APTT (sec).

In the deficient type, as shown by a polygonal line (a) obtained by connecting points each plotted in a circle in FIG. 1, APTT is corrected by adding normal plasma, and a pattern protruding downward is shown. On the other hand, in the inhibitor type, as shown by a polygonal line (b) obtained by connecting points each plotted in a square shape in FIG. 1, APTT is less likely to be corrected even when normal plasma is added, and a pattern protruding upward is shown. However, a reaction of an inhibitor to a VIII factor has a dependence on a time and a temperature, and therefore, a shape protruding upward is not clearly shown in the reaction immediately after mixing (hereinafter, referred to as an "immediate reaction"), and a shape protruding upward may be shown in a reaction after incubation at 37° C. for a certain period of time (hereinafter, referred to as a "delay reaction"). Accordingly, in the cross-mixing test, it is recommended to determine both the immediate reaction and the delay reaction.

Embodiments of the invention will be described below.

Embodiment 1

FIG. 2 is an overall schematic configuration diagram of an automatic analysis device 100. As shown in FIG. 2, the automatic analysis device 100 includes a specimen dispensing mechanism 101, a specimen disk 102, a reagent dispensing mechanism 106, a reagent disk 107, a reaction container stock unit 111, a reaction container transport mechanism 112, a detection unit 113, a reaction container discarding unit 117, an input and output unit 118, a storage unit 119, and a control unit 120.

The specimen dispensing mechanism 101 aspirates a specimen accommodated in a specimen container 103 disposed in the specimen disk 102 rotating clockwise and counterclockwise, and discharges the specimen to a reaction container 104 accommodated in the reaction container stock unit 111. The specimen dispensing mechanism 101 includes a specimen dispensing probe 101a at a distal end portion thereof, and performs aspiration and discharge of a specimen based on an operation of a specimen syringe pump 105 controlled by the control unit 120.

The reagent dispensing mechanism 106 aspirates a reagent accommodated in a reagent container 108 disposed in the reagent disk 107, and discharges the reagent to a reaction container 104 accommodated in the reaction container stock unit 111. The reagent dispensing mechanism 106 includes a reagent dispensing probe 106a at a distal end portion thereof, and performs aspiration and discharge of the reagent based on an operation of a reagent syringe pump 110 controlled by the control unit 120. The reagent dispensing mechanism 106 includes a built-in reagent heating mechanism 109, and the reagent aspirated by the reagent dispensing mechanism 106 is heated to a predetermined temperature by the reagent heating mechanism 109.

The reaction container transport mechanism 112 transports and places the reaction container 104 accommodated in the reaction container stock unit 111. The reaction container transport mechanism 112 transports and places the reaction container 104 from the reaction container stock unit 111 to a reaction container placing unit 114 of the detection unit 113 by gripping and pivoting the reaction container 104 in a horizontal direction. The reaction container transport mechanism 112 grips a reaction container 104 for which the measurement is completed, and discards the reaction container 104 to the reaction container discarding unit 117.

The detection unit 113 (measurement unit) includes the reaction container placing unit 114 for placing the reaction container 104, a light source 115, and a light receiving unit 116. The detection unit 113 measures a light intensity of a specimen in the reaction container 104 inserted into the reaction container placing unit 114. The present embodiment describes a configuration in which one detection unit 113 is disposed, and a configuration in which a plurality of detection units 113 are disposed may be used.

An example of the detection principle in the detection unit 113 will be described below. The light emitted from the light source 115 is scattered by a reaction solution (specimen) in the reaction container 104. The light receiving unit 116 includes a photodiode or the like. The light receiving unit 116 receives the scattered light scattered by the reaction solution in the reaction container 104 and performs photoelectric conversion to output a photometric signal indicating an intensity of the received scattered light to an A/D converter 121. A measurement signal of the scattered light subjected to the A/D conversion by the A/D converter 121 is input to the control unit 120 via an interface 122.

The light receiving unit 116 is not limited to the configuration in which the intensity of the scattered light scattered by the reaction solution in the reaction container 104 is detected. For example, the light receiving unit 116 may have a configuration in which an intensity of transmitted light passing through the reaction solution in the reaction container 104 is detected. The light receiving unit 116 capable of detecting both scattered light and transmitted light may be used. The light receiving unit 116 may use a viscous degree.

The control unit 120 includes an analysis operation control unit 120a, a coagulation time calculation unit 120b, and a graph creation unit 120c. The functions of the analysis operation control unit 120a, the coagulation time calculation unit 120b, and the graph creation unit 120c are implemented by reading a program stored in a ROM or a storage unit 119 (not shown) and executing the read program by a processor such as a CPU.

The analysis operation control unit 120a controls the specimen dispensing mechanism 101 and the specimen disk 102 to dispense test plasma and/or normal plasma added to correct the coagulation time of the test plasma into a plurality of specimen containers 103. The analysis operation control unit 120a controls the specimen dispensing mechanism 101 and the specimen disk 102 to dispense each of prepared specimens containing only the test plasma, only the normal plasma, or mixed plasma obtained by mixing the test plasma and the normal plasma from the specimen container 103 to the reaction container 104. The analysis operation control unit 120a controls the reagent dispensing mechanism 106 and the reagent disk 107 to dispense the reagent into the reaction container 104. The analysis operation control unit 120a controls the detection unit 113 to emit light from the light source 115 to the prepared specimen to which the reagent in the reaction container 104 is added, and to measure a light intensity of the obtained scattered light. In addition, the analysis operation control unit 120a controls the reagent heating mechanism 109 to heat the reagent to a predetermined temperature, or controls the reaction container transport mechanism 112 to transport, place, and discard the reaction container 104.

The coagulation time calculation unit 120b calculates a coagulation time based on the light intensity measured by the detection unit 113. The graph creation unit 120c creates a graph related to the coagulation time of each of the prepared specimens calculated by the coagulation time calculation unit 120b.

The input and output unit 118 includes a mouse 118a and a keyboard 118b, which are input units, and a display 118c

(display unit), which is an output unit. When an operator inputs an analysis item of a specimen to be analyzed by the automatic analysis device 100 using the input unit, the input information is transmitted to the control unit 120. The display unit displays an analysis result, an alarm, and the like, and also displays a coagulation time calculated by the coagulation time calculation unit 120b and a graph created by the graph creation unit 120c.

The storage unit 119 stores an analysis result, a coagulation time, and the like. The analysis result, the coagulation time, and the like may be printed out by the printer 123 connected to the input and output unit 118 via the interface 122.

In FIG. 2, the reaction container stock unit 111, the specimen disk 102, and the reagent disk 107 appear to be spaced apart from one another for the sake of convenience in showing all the components. However, actually, the specimen disk 102 and the reaction container stock unit 111 are disposed within a range of an arc-shaped movement locus of the specimen dispensing probe 101a constituting the specimen dispensing mechanism 101. The reagent disk 107 and the reaction container stock unit 111 are disposed within a range of an arc-shaped movement locus of the reagent dispensing probe 106a constituting the reagent dispensing mechanism 106. Accordingly, when the automatic analysis device 100 is viewed from above, the specimen disk 102, the reaction container stock unit 111, and the reagent disk 107 are disposed in a substantially triangle shape. In order to improve the processing capability, the automatic analysis device 100 may further include an incubator 124 for increasing the temperature of a specimen at the start of the measurement before the reagent is added.

Next, a method for preparing a specimen used in the cross-mixing test will be described with reference to FIGS. 3 and 4. FIG. 3 is a flowchart showing a method for preparing mixed plasma used in the cross-mixing test. FIG. 4 shows an example of a preparation setting screen of mixed plasma used in the cross-mixing test.

The operator checks a request for the cross-mixing test (hereinafter, may be simply referred to as measurement) (step S300), and prepares a specimen (step S301). Next, the operator sets a test item and a ratio of the test plasma in each of the immediate type and the delay type using the input unit while viewing the setting screen shown in FIG. 4 output to the display unit (step S302). The ratio of the test plasma may be stored in the storage unit 119 in advance before the measurement request, or may be changed every time the measurement is performed.

The analysis operation control unit 120a calculates a normal plasma volume and a test plasma volume required for the measurement based on the test item and the test plasma ratio set in step S302, and displays the calculated normal plasma volume and the calculated test plasma volume on the setting screen in FIG. 4 (step S303). As described above, the operator is notified of the required normal plasma volume and the required test plasma volume via the display unit, and therefore, not only the burden of the operator to calculate the required amount can be reduced, but also the plasma volume can be prevented from being insufficient during the preparation.

Next, the operator sets a placement position for a specimen container 103a filled with the normal plasma, a placement position for a specimen container 103b filled with the test plasma, and a placement position for each of empty specimen containers 103c to 103g (step S304). Here, each position represents a placement position for the specimen container 103 in the specimen disk 102. Each position is not necessarily specified by numbers alone, and may be, for example, a combination of alphabets and numbers. In addition, each position may be automatically set by the analysis operation control unit 120a instead of being set by the operator.

The operator respectively places the specimen container 103a filled with the normal plasma, the specimen container 103b filled with the test plasma, and the empty specimen containers 103c to 103g at the positions set in step S304 (step S305). The analysis operation control unit 120a calculates the time required for preparing the mixed plasma and outputs the time to the display unit (step S306). Next, the analysis operation control unit 120a executes the container placement check, that is, executes check of whether there is an empty specimen container and whether a required amount of normal plasma or test plasma is present (step S307).

FIG. 5 is a diagram showing a state when the specimen dispensing mechanism 101 checks the presence or absence of an empty specimen container. As shown in FIG. 5, the presence or absence of an empty specimen container is checked based on whether a physical abnormality is detected when the specimen dispensing probe 101a provided at a distal end of the specimen dispensing mechanism 101 comes into contact with a bottom of the empty specimen container.

On the other hand, whether there is a required amount of normal plasma and abnormal plasma is checked by using a liquid surface detection function of the specimen dispensing mechanism 101. The liquid surface detection function refers to a function of detecting a liquid surface by capturing an electrical characteristic such as a static capacitance or a resistance value which changes when the specimen dispensing probe 101a provided at the distal end of the specimen dispensing mechanism 101 comes into contact with or approaches the liquid surface. When the amount of the normal plasma is to be checked, the analysis operation control unit 120a rotates the specimen disk 102 such that the specimen container 103a filled with the normal plasma among the specimen containers 103 placed in the specimen disk 102 is positioned at a dispensing position (see FIG. 6 described below) of the specimen dispensing mechanism 101. Thereafter, the analysis operation control unit 120a checks the amount of the normal plasma in the specimen container 103a based on the liquid surface detection function of the specimen dispensing probe 101a. When the amount of the test plasma is to be checked, the analysis operation control unit 120a rotates the specimen disk 102 such that the specimen container 103b filled with the test plasma among the specimen containers 103 placed in the specimen disk 102 is positioned at a dispensing position (see FIG. 7 described below) of the specimen dispensing mechanism 101. Thereafter, the analysis operation control unit 120a checks the amount of the test plasma in the specimen container 103b based on the liquid surface detection function of the specimen dispensing probe 101a.

If it is determined in step S307 that the normal plasma volume or the test plasma volume does not satisfy the required amount or a required number of empty specimen containers are not placed in a predetermined position, the analysis operation control unit 120a stops the preparation of the mixed plasma and outputs a system alarm to the display unit (step S308). Accordingly, it is possible to avoid contamination of the specimen disk 102 caused by the shortage of plasma during preparation and measurements or caused by performing dispensing in a place where the empty specimen container is not placed, mixing due to further dispensing in a specimen container into which a specimen (normal plasma, test plasma, mixed plasma) has been dispensed, and the like. In the system alarm, sound may also be output (the same applies to the following system alarm).

On the other hand, if it is determined in step S307 that the normal plasma volume and the test plasma volume satisfy the required amount and the required number of empty specimen containers are placed, the analysis operation control unit 120a starts the dispensing of the normal plasma to the empty specimen containers 103c to 103g (step S309).

Here, the operation of dispensing the normal plasma will be described. First, with rotation of the specimen disk 102, as shown in FIG. 6, the specimen container 103a filled with the normal plasma is moved to the dispensing position for the specimen dispensing mechanism 101, and then, the specimen dispensing probe 101a of the specimen dispensing mechanism 101 aspirates the normal plasma. In the present embodiment, it is assumed that the specimen disk 102 rotates clockwise in a stepwise manner, and the movement distance in each step corresponds to a pitch between two specimen containers 103 disposed adjacent to each other.

Thereafter, the specimen disk 102 is further rotated, and as shown in FIG. 7, the specimen container 103b filled with the test plasma is moved to the dispensing position for the specimen dispensing mechanism 101. At this time, the specimen dispensing mechanism 101 does not discharge the normal plasma aspirated from the specimen container 103a to the specimen container 103b.

Next, the specimen disk 102 is further rotated, as shown in FIG. 8, the empty specimen container 103c is moved to the dispensing position for the specimen dispensing mechanism 101, and then, the specimen dispensing probe 101a of the specimen dispensing mechanism 101 discharges the normal plasma to the empty specimen container 103c. At this time, it is assumed that the distal end of the specimen dispensing probe 101a is at a height at which the distal end does not come into contact with the liquid surface of the normal plasma discharged into the specimen container 103c. Thereafter, when the specimen dispensing probe 101a is lowered and the liquid surface is detected by the liquid surface detection function, the specimen dispensing probe 101a rises. This operation allows the normal plasma adhering to the distal end of the specimen dispensing probe 101a to be moved into the specimen container 103c. The contamination caused by the plasma on the specimen dispensing probe 101a can be restricted to the minimum limit.

This operation is repeated, and when the normal plasma is dispensed into the empty specimen containers 103d to 103g, the analysis operation control unit 120a determines whether all the dispensing of the normal plasma is completed (step S310). If it is determined in step S310 that the dispensing of the normal plasma is not completed, the analysis operation control unit 120a stops the preparation of the mixed plasma and outputs the system alarm to the display unit (step S311). On the other hand, if it is determined in step S310 that the dispensing of the normal plasma is completed, the analysis operation control unit 120a then starts to dispense the test plasma (step S312).

Here, the operation of dispensing the test plasma will be described. First, with rotation of the specimen disk 102, the specimen container 103b filled with the test plasma is moved to the dispensing position for the specimen dispensing mechanism 101, and then the specimen dispensing probe 101a of the specimen dispensing mechanism 101 aspirates the test plasma.

Thereafter, the specimen disk 102 is further rotated, the specimen container 103c to which the normal plasma is discharged in step S309 is moved to the dispensing position for the specimen dispensing mechanism 101, and then, the specimen dispensing probe 101a of the specimen dispensing mechanism 101 discharges the test plasma to the specimen container 103. At this time, it is assumed that the distal end of the specimen dispensing probe 101a is at a height at which the distal end does not come into contact with a liquid surface of the test plasma discharged into the specimen container 103c. Thereafter, when the specimen dispensing probe 101a is lowered and the liquid surface is detected by the liquid surface detection function, the specimen dispensing probe 101a rises. This operation allows the test plasma adhering to the distal end of the specimen dispensing probe 101a to be moved into the specimen container 103c. The specimen dispensing probe 101a can also be prevented from being contaminated by the normal plasma and the test plasma.

When the test plasma is dispensed into the specimen container 103c, the specimen dispensing mechanism 101 stirs mixed plasma formed of the normal plasma and the test plasma in the specimen container 103c (step S313). For example, the specimen dispensing probe 101a stirs the mixed plasma in the specimen container 103 using a discharge pressure of the specimen syringe pump 105 while repeatedly aspirating and discharging the mixed plasma. The specimen dispensing probe 101a is also lowered in accordance with the drop of the liquid surface during the aspiration, and the specimen dispensing probe 101a also rises in accordance with the rise of the liquid surface during the discharge. This operation can restrict the contamination caused by the plasma on the specimen dispensing probe 101a to the minimum limit. For this stirring method, it is not required to provide a dedicated component for stirring, and therefore, the automatic analysis device 100 can be reduced in space. In this case, the mixed plasma may be stirred by, for example, another stirring method such as a stirring method using ultrasonic waves.

With respect to the specimen containers 103d to 103g to which the normal plasma is discharged in step S309, the test plasma is dispensed in the same procedure as the specimen container 103c, and the mixed plasma is stirred by the specimen dispensing probe 101a. After this operation is repeated, the analysis operation control unit 120a determines whether all the dispensing and stirring of the test plasma are completed (step S314).

If it is determined in step S314 that the dispensing of the test plasma and the stirring of the mixed plasma are not completed, the analysis operation control unit 120a stops the dispensing and stirring and outputs the system alarm to the display unit (step S315). On the other hand, if it is determined in step S314 that the dispensing and stirring are completed, the analysis operation control unit 120a notifies the display unit that the preparation of the mixed plasma is completed (step S316).

The volume of the normal plasma discharged from the specimen dispensing probe 101a in step S309 and the volume of the test plasma discharged from the specimen dispensing probe 101a in step S312 are automatically calculated by the analysis operation control unit 120a based on the test plasma ratio set in step S302. When the dispensing amount with respect to one empty specimen container exceeds the maximum dispensing amount of the specimen dispensing probe 101a, the specimen dispensing mechanism 101 performs dispensing in several times. The number of times of the dispensing is also automatically calculated by the analysis operation control unit 120a.

In the flowchart shown in FIG. 3, the dispensing of the test plasma is performed (step S312) after the dispensing of the normal plasma (step S309). Conversely, the dispensing of normal plasma may be performed after the dispensing of the test plasma. In the flowchart shown in FIG. 3, from the viewpoint of preventing contamination of the normal plasma and the test plasma, the dispensing of the normal plasma and the dispensing of the test plasma are performed independently, but the invention is not limited thereto. For example, when cleaning of the specimen dispensing mechanism 101 is sufficient and there is no concern of contamination, the mixed plasma may be prepared one by one. In this case, after dispensing the required amount of normal plasma into the empty specimen container 103c, the specimen dispensing mechanism 101 dispenses the required volume of test plasma into the specimen container 103c before dispensing the normal plasma into the next specimen container 103d. Then, when the preparation of the mixed plasma in the specimen container 103c is completed, the specimen dispensing mechanism 101 performs the preparation of the mixed plasma in the empty specimen container 103d and then sequentially prepares the mixed plasma for each empty specimen container.

Next, processing until a graph for the cross-mixing test is created using the prepared specimen will be described in detail. FIG. 9 is a flowchart showing a method for measuring a prepared specimen and creating a graph. In the cross-mixing test, first, the measurement of the immediate type is performed using mixed plasma immediately after the preparation is completed, and then the measurement of the delay type is performed using mixed plasma after the preparation is completed and then incubation is performed for a certain period of time. Hereinafter, details will be described.

When the preparation of the mixed plasma is completed, the analysis operation control unit 120a not only outputs the fact to the display unit as in step S316 shown in FIG. 3, but also outputs information for checking whether to perform the measurement of the immediate type (step S901). FIG. 10 shows an example of a screen for preparation completion notification and immediate type measurement check. In the example shown in FIG. 10, it is assumed that the mixed plasma automatically prepared by the automatic analysis device 100 according to the flow shown in FIG. 3 is used for the measurement of the immediate type as it is. Alternatively, mixed plasma prepared outside the automatic analysis device 100, for example mixed plasma prepared manually by an operator, may be used for the measurement of the immediate type.

When the operator makes an instruction of the measurement of the immediate type using the input unit (step S902), the measurement unit measures the scattered light intensity of each of the prepared specimens for a predetermined time, and the coagulation time calculation unit 120b calculates a coagulation time of each mixed plasma based on the measurement result (step S903).

As a method for calculating the coagulation time, as shown in Patent Literature [JPH06-27115A], a method for using the light amount as it is, a method for using a derivative of the scattered light amount, and the like are known. Here, the coagulation time calculation unit 120b calculates the coagulation time based on the method for using the light amount as it is. Hereinafter, the method for using the light amount as it is will be specifically described.

First, the coagulation time calculation unit 120b generates a coagulation reaction curve indicating a change in the scattered light intensity over time based on measurement data obtained by the detection unit 113. FIG. 11 shows an example of a coagulation reaction curve. As shown in FIG. 11, there is almost no change in the scattered light intensity at the start of measurement immediately after reagent addition. Thereafter, as coagulation progresses, the specimen becomes cloudy and a rapid increase in the scattered light intensity is observed. When the coagulation reaction is substantially completed, the change in the scattered light intensity is small and then is substantially constant. The coagulation time calculation unit 120b calculates, based on a scattered light intensity at a time point when a certain specified time has elapsed from a reagent mixing time point $T_0$, a difference between the scattered light intensity at the time point when the specified time has elapsed (coagulation reaction end level) and a scattered light intensity at $T_0$ (coagulation reaction start level), and time T from $T_0$ to a time point when the scattered light intensity is increased by 1/N (N is a predetermined number equal to or greater than 1) of the difference is defined as the coagulation time. In other words, the coagulation time calculation unit 120b calculates a reference intensity difference which is an intensity difference between the light intensity at the coagulation reaction start level and the light intensity at the coagulation reaction end level, and calculates, as the coagulation time, the time until the intensity difference with the coagulation reaction start level reaches the predetermined ratio with respect to the reference intensity difference. In the present embodiment, this method is called the percentile method.

Returning to the description in FIG. 9, after the coagulation time is calculated in step S903, the graph creation unit 120c creates a graph of the immediate type based on the coagulation time of each mixed plasma calculated by the coagulation time calculation unit 120b (step S904), and the graph is output to the display unit.

The operator checks the graph of the immediate type (step S905) and subsequently performs the measurement of the delay type. In this case, a container for each mixed plasma after the measurement of the immediate type is closed, and incubation is performed at 37° C. for 2 hours (step S906). Here, a case where the incubation is performed outside the automatic analysis device 100 will be described, and in a case where the automatic analysis device 100 has an incubator, incubation may be performed within the device. When the incubation is completed, the operator opens containers for mixed plasma and places the containers on the specimen disk 102 (step S907).

Thereafter, when the operator makes an instruction of the measurement of the delay type using the input unit (step S908), the measurement unit measures a scattered light intensity of each mixed plasma for a predetermined time, and the coagulation time calculation unit 120b calculates a coagulation time of each mixed plasma based on the measurement result (step S909). Further, the graph creation unit 120c creates a graph of the delay type based on the coagulation time of each mixed plasma calculated by the coagulation time calculation unit 120b (step S910). The graph created by the graph creation unit 120c is output to the display unit, and the operator checks the graph (step S911).

When the measurements of the immediate type and the delay type are completed, a measurement result output screen (no error) as shown in FIG. 12 is output to the display unit. The operator refers to a polygonal line (A) for the immediate type, which connects points each plotted in a circle in FIG. 12, and a polygonal line (B) for the delay type, which connects points each plotted in a square shape in FIG. 12. The calculation results of the value obtained by (measurement result of test plasma ratio of 50%-measurement result of test plasma ratio of 0%)/(measurement result of test plasma ratio of 100%)×100 on the immediate type and the delay type are also displayed as Rosner Index (index of circulation anticoagulant: ICA) on the screen in FIG. 12.

Accordingly, a shape of the graph can be represented by numerical values, and Rosner Index can be used as one of the indexes for objective evaluation.

Here, when there is mixed plasma for which the coagulation time cannot be calculated for several causes, the measurement result of the mixed plasma is an error, and a graph cannot be displayed. When a predetermined determination condition is not satisfied even though the coagulation time can be calculated, the reliability of the measurement result may not be guaranteed. Therefore, an alarm or the like may also be displayed in combination with the measurement results of the mixed plasma. When the operator designates a measurement result of the predetermined mixed plasma on the screen shown in FIG. 12, the display unit makes a display to urge the operator to delete the measurement result from the graph creation targets. At this time, when the operator performs an operation (selection) to delete the measurement result from the graph, the graph creation unit 120c deletes the designated measurement result and creates a graph using only measurement results of the other mixed plasma. Accordingly, even if an error or the like occurs in a measurement result of a part of the mixed plasma, the operator can perform determination according to the cross-mixing test.

When the mixed plasma prepared by the automatic analysis device 100 includes plasma for which the coagulation time cannot be calculated, the graph creation unit 120c may create a graph using a coagulation time calculated for the mixed plasma prepared outside the automatic analysis device 100.

FIG. 13 shows an example of a selection screen for a measurement result used for creating a graph. In the example shown in FIG. 13, a case where APTT is selected as a test item is shown. As the test item, in addition to APTT, a prothrombin time (PT), dilution PT (dPT), dilution APTT (dAPTT), a kaolin coagulation time (KCT), and a dilute russell's viper venom time (dRVVT) may also be selected. All measurement results related to APTT are displayed in a left column, and in addition to the coagulation time, the specimen ID, the date and time, the comment (1), and the comment (2) are also displayed for each measurement result. The comment (1) includes information on whether the measurement is a measurement using mixed plasma automatically prepared in the automatic analysis device 100 or a measurement using mixed plasma manually prepared outside the automatic analysis device 100. On the other hand, the comment (2) includes information such as the test plasma ratio, the immediate type, or the delay type. The comment (1) and the comment (2) may be input by the operator using the input unit or may be automatically input by the analysis operation control unit 120a.

When the operator taps a right-pointing arrow button in a state in which a desired measurement result in the left column is selected, the measurement result is added to an upper right column or a lower right column as the measurement result used for creating a graph. A measurement result for the immediate type is displayed in the upper right column, and a measurement result for the delay type is displayed in the lower right column.

Therefore, when an error is included in a part of the measurement result using the mixed plasma prepared in the automatic analysis device 100, a graph can be created by replacing the measurement result including the error with the measurement result using the mixed plasma prepared outside the automatic analysis device 100. For example, after an error occurs in the measurement result for the mixed plasma having the predetermined test plasma ratio, which is automatically prepared for the immediate type, the operator manually prepares mixed plasma having the test plasma ratio of the error target. When the coagulation time calculation unit 120*b* can measure the coagulation time using the prepared specimen, the measurement result is displayed in the left column of the selection screen shown in FIG. 13. As a result, even if an error occurs, a graph can be created in a relatively short time.

However, when there is an error in a part of the measurement result for the delay type, incubation for a certain period of time is required even after manual preparation. Therefore, it takes a relatively long time to remeasure the coagulation time. For example, in a case where an error occurs if the coagulation time when the test plasma ratio is 100% exceeds a certain period of time, an error may occur again even if the coagulation time is measured again. In such a case, it is desirable to create a graph by estimating the coagulation time of the prepared specimen in which an error has occurred. Even when an error occurs in the measurement result for the delay type, the manually prepared mixed plasma may be used. Even when an error occurs in the measurement result for the immediate type, the coagulation time may be estimated.

When a prepared specimen for which the coagulation time cannot be calculated due to the error is present, the coagulation time calculation unit 120*b* in the present embodiment estimates the coagulation time. Hereinafter, a method for estimating the coagulation time by the coagulation time calculation unit 120*b* will be described. In the present embodiment, errors with which the coagulation time calculation unit 120*b* cannot calculate the coagulation time although the light intensity is measured by the detection unit 113 are targeted, and errors that occur before the light intensity is measured, such as errors due to a shortage of specimen or reagent, are not targeted.

FIG. 14 is a flowchart showing the method for estimating the coagulation time by the coagulation time calculation unit 120*b* in Embodiment 1. First, the coagulation time calculation unit 120*b* determines whether there is an error (step S1401), and if there is an error, the coagulation time calculation unit 120*b* determines whether a scattered light intensity of a prepared specimen as an error target has reached a coagulation reaction end level (step S1402).

In step S1402, if the scattered light intensity does not reach the coagulation reaction end level, that is, if a prepared specimen for which the measurement of a light intensity is ended before the coagulation reaction end level is reached is present, the coagulation time calculation unit 120*b* estimates the reference intensity difference of the prepared specimen using a reference intensity difference of another prepared specimen (step S1403).

Here, a method for estimating the reference intensity difference will be described. An amount of change in the light intensity from the start of the coagulation reaction to the end of the coagulation reaction correlates with the fibrinogen concentration. That is, when the test plasma ratio of the mixed plasma is plotted on a horizontal axis and the reference intensity difference is plotted on a vertical axis, a substantially linear correlation can be obtained. The coagulation time calculation unit 120*b* uses this property to determine an approximate expression of a primary straight line using, for example, the least square method based on the reference intensity difference data of another prepared specimen that is not an error target. Further, the coagulation time calculation unit 120*b* estimates the reference intensity difference of the prepared specimen as the error target using the approximate expression. Whether another prepared specimen used for estimating the reference intensity is a delay type or an immediate type or where the other prepared specimen is performed does not matter.

Next, the coagulation time calculation unit 120*b* estimates the light intensity of the prepared specimen as the error target at the coagulation reaction end level using the reference intensity difference estimated in step S1403 (step S1404). The light intensity at the coagulation reaction end level is determined by the following (Formula 1).

[Math. 1]

$$
\begin{array}{l}
\text{LIGHT INTENSITY} \\
\text{AT COAGULATION} = \\
\text{REACTION END LEVEL}
\end{array}
\qquad \text{(FORMULA 1)}
$$

$$
\begin{array}{ccc}
\text{LIGHT INTENSITY} & & \text{REFERENCE} \\
\text{AT COAGULATION} & + & \text{INTENSITY} \\
\text{REACTION START LEVEL} & & \text{DIFFERENCE}
\end{array}
$$

Thereafter, the coagulation time calculation unit 120*b* determines whether a coagulation reaction curve is obtained until the light intensity exceeds a predetermined value % from the coagulation reaction start level, that is, whether there is a prepared specimen for which the measurement of the light intensity is ended before a predetermined ratio is reached with respect to the estimated reference intensity difference (step S1405). When a coagulation reaction curve exceeding the predetermined value % (P %) is obtained, the coagulation time calculation unit 120*b* estimates the coagulation time from a time point corresponding to the light intensity at the predetermined value % (P %) obtained by the following (Formula 2) (step S1406).

[Math. 2]

$$
\begin{array}{l}
\text{LIGHT} \\
\text{INTENSITY} = \\
\text{AT } P \text{ \%}
\end{array}
\qquad \text{(FORMULA 2)}
$$

$$
\begin{array}{ccc}
\text{LIGHT INTENSITY} & & \text{REFERENCE} \\
\text{AT COAGULATION} & + & \text{INTENSITY} \times P \div 100 \\
\text{REACTION START LEVEL} & & \text{DIFFERENCE}
\end{array}
$$

Regarding the coagulation time estimated by the coagulation time calculation unit 120*b*, a measurement result output screen (with an error) as shown in FIG. 15 is output to the display unit (step S1409). In the example shown in FIG. 15, the measurement result for the delay type with the test plasma ratio of 100% is an error. Therefore, the measurement result is replaced with an estimation result obtained by the coagulation time calculation unit 120*b*. As described above, the coagulation time estimated due to the error is displayed separately from the coagulation time calculated without error (in the example shown in FIG. 15, with the annotation of "recalculation"). Therefore, the operator can understand the accuracy of the coagulation time, and the reliability of the cross-mixing test is increased.

On the other hand, in step S1405, when the coagulation reaction curve exceeding the predetermined value % is not obtained, the estimation of the coagulation time by the percentile method is not possible. Therefore, the coagulation time calculation unit 120*b* attempts to estimate the coagulation time according to the method using the derivative of the scattered light amount.

Here, the method using the derivative of the scattered light amount will be specifically described. Similarly to the percentile method described above, the coagulation time calculation unit 120*b* generates a coagulation reaction curve indicating a change in the scattered light intensity over time based on the measurement data obtained by the detection unit 113. Thereafter, the coagulation time calculation unit 120*b* sets the coagulation time to a time up to a time point when the first derivative of the scattered light intensity reaches a peak. In the present embodiment, this method is referred to as a first derivative method. Although this method has a lower accuracy in calculating the coagulation time than the percentile method, the method has the advantage that the coagulation time can be calculated even when the coagulation reaction end level is unknown.

The coagulation time calculation unit 120*b* according to the present embodiment first attempts to calculate and estimate the coagulation time by preferentially using the percentile method, and estimates the coagulation time using the first derivative method when the estimation using the percentile method is not possible. However, the first derivative method may be preferentially used. In this description, the case where the light intensity reaches the coagulation reaction end level and the coagulation time calculation unit 120*b* calculates a highly accurate coagulation time using the percentile method may be referred to as "calculation (of coagulation time)". On the other hand, the case where the light intensity does not reach the coagulation reaction end level and the coagulation time calculation unit 120*b* calculates the coagulation time based on the first derivative method, or the case where the coagulation time calculation unit 120*b* calculates a virtual coagulation time by using the measurement result of another prepared specimen that has reached the coagulation reaction end level, as described below, may be referred to as "estimation of (coagulation time)".

Returning to the description in FIG. 14, based on the first derivative method, the coagulation time calculation unit 120*b* determines whether there is a measurement timing i at which $A_i > A_{i+1}$ is satisfied after the coagulation reaction start level when $A_i$ represents a coagulation reaction rate which is the first derivative of the coagulation reaction curve (step S1407). When no measurement timing i satisfying this condition is present, that is, when no peak is present in the first derivative of the light intensity, the estimation of the coagulation time by the first derivative method is not possible, and therefore, an error is output to the display unit.

In step S1407, when the measurement timing i satisfying the condition is present, that is, when a peak is present in the first derivative of the light intensity, the coagulation time calculation unit 120*b* estimates the time until the first derivative of the light intensity reaches the peak as the coagulation time (step S1408). The coagulation time estimated in step S1408 is output to the display unit (step S1409). The first derivative method is fundamentally different from the percentile method in a calculation method, and therefore, when the first derivative method is used, it is required to estimate the coagulation time for all the prepared specimens used in the cross-mixing test using the first derivative method.

According to the present embodiment, when an error occurs in a part of the measurement result, the determination using the cross-mixing test can be performed without re-preparation of the specimen or re-measurement of the light intensity. When the re-preparation of the specimen is not required, the plasma volume can be saved, which leads to a reduction in a patient burden due to recollection. When the re-measurement of the light intensity is not required, the time required for the cross-mixing test is shortened. Further, in the present embodiment, even when the estimation of the coagulation time according to the percentile method is not possible, the possibility of performing the cross-mixing test is further increased because the coagulation time is estimated according to the first derivative method. When the estimated coagulation time is output, it is desirable to clearly indicate whether the estimation method is a percentile method or a first derivative method.

Further, the coagulation time calculation unit 120*b* according to the present embodiment first attempts to calculate and estimate the coagulation time by preferentially using the percentile method, and estimates the coagulation time using the first derivative method when the estimation using the percentile method is not possible. In this case, as the calculation method for the coagulation time by the coagulation time calculation unit 120*b*, a display to prompt the switching to the percentile method or the first derivative method as shown in FIG. 15 is made, and the calculation method may be switched by the operation of the operator.

Embodiment 2

In Embodiment 2, a part of the method for estimating the coagulation time by the coagulation time calculation unit 120*b* is different from that of Embodiment 1. In Embodiment 1, when a prepared specimen for which the measurement of the light intensity is completed before the coagulation reaction end level is reached has been present, the coagulation time of the prepared specimen is estimated by estimating the reference intensity difference of the prepared specimen using the reference intensity difference of another prepared specimen. However, in Embodiment 2, the coagulation time of the prepared specimen is estimated by estimating a coagulation reaction curve using a second derivative of the light intensity measured by the detection unit 113.

FIG. 16 shows a second derivative curve of a general APTT measurement result. In the present embodiment, the second derivative of the scattered light intensity is used for determining a plateau of the coagulation reaction curve. Therefore, a start point of the coagulation reaction and an end point of the coagulation reaction can be regarded as time points at which the second derivative of the scattered light intensity becomes approximately zero. The second derivative curve reaches a minimum value after reaching a peak value, and the time from the start of the coagulation reaction until the minimum value is reached is defined as $T_{min}$.

FIG. 17 is a flowchart showing a method for estimating the coagulation time by the coagulation time calculation unit 120*b* in Embodiment 2. First, the coagulation time calculation unit 120*b* determines whether there is an error (step S1701), and if there is an error, the coagulation time calculation unit 120*b* determines whether $T_{min}$ is present in a measurement result of the prepared specimen as an error target (step S1702).

In step S1702, if it is determined that $T_{min}$ is present, the coagulation time calculation unit 120*b* estimates a second derivative curve (step S1703).

Here, the method for estimating the second derivative curve will be described. For example, in a specimen in which the test plasma ratio is 100' and the coagulation time is extremely long, the measurement may be ended without reaching the plateau after $T_{min}$. In this case, the coagulation time calculation unit 120*b* creates an estimation curve by fitting a logistic curve of the following (Formula 3) to the second derivative curve after $T_{min}$ and a point $(t, y) = (T_{min} + 600, 0)$.

[Math. 3]

$$y = \frac{a}{1 + \left(\frac{t}{b}\right)^k} + c \qquad \text{(FORMULA 3)}$$

In (Formula 3), t represents a time, y represents a second derivative, and a, b, and c represent parameters. The coagulation time calculation unit 120b calculates values of the parameters in an approximation function of (Formula 3) such that a difference between a time-second derivative approximation curve expressed by the approximation function and the second derivative is as small as possible. For example, the values of the parameters are determined by using regression analysis such that a square error between the time-series light intensity data and the light intensity calculated by the approximation function is as small as possible.

When the second derivative curve is estimated in step S1703, the coagulation time calculation unit 120b determines the time until the estimation curve reaches the plateau, and sets the determined time as the reaction end time (step S1704).

Next, the coagulation time calculation unit 120b restores the first derivative every 0.1 seconds from the measurement end time using the following (Formula 4) (step S1705).

[Math. 4]

$$F(t + 0.1) = F(t) + y(t) \qquad \text{(FORMULA 4)}$$

In (Formula 4), F represents a primary partial value. When the first derivative is restored up to the reaction end time, the coagulation time calculation unit 120b completes the restoration.

Further, the coagulation time calculation unit 120b restores the coagulation reaction curve from the first derivative by the same method (step S1706).

Thereafter, the coagulation time calculation unit 120b estimates the coagulation time based on the coagulation reaction curve restored in step S1706 according to the percentile method described in Embodiment 1 (step S1707). The subsequent steps are the same as those of Embodiment 1.

On the other hand, if it is determined in step S1702 that $T_{min}$ is not present, the coagulation time calculation unit 120b attempts to estimate the coagulation time by the first derivative method. The subsequent steps are the same as those of Embodiment 1.

According to the present embodiment, the same effects as those of Embodiment 1 can be obtained. Further, the estimation of the coagulation time by the estimation curve of the second derivative curve according to the present embodiment can be used for analysis other than the cross-mixing test.

Embodiment 3

In Embodiment 3, a specimen to be subjected to the cross-mixing test is managed by a test ID. A configuration of an automatic analysis device and the processing related to the calculation of the coagulation time according to Embodiment 3 are the same as those of Embodiment 1. Therefore, the differences from the Embodiment 1 are described below.

In addition, the method for estimating the coagulation time may be the same as that of Embodiment 1 or Embodiment 2.

FIG. 18 shows an example of a mixed plasma adjustment setting screen according to Embodiment 3. As shown in FIG. 18, the mixed plasma adjustment setting screen includes a test ID input field in the present embodiment. When the operator inputs a test ID for identifying the specimen to be subjected to the cross-mixing test, it is possible to manage, with one test ID, the measurement result for each of the plasma ratios of the immediate type and the delay type output thereafter. Here, the test ID may be any character string. When the test plasma is marked with a bar code or RFID, the test ID can also be recognized by reading the request information from a host using a reading unit such as a handy bar code reader or an RFID reader of the automatic analysis device 100, instead of inputting the test ID from the operation screen.

A method for associating the test ID and the measurement result will be described. In FIG. 18, a placement position for the specimen container 103a filled with the normal plasma, a placement position for the specimen container 103b filled with the test plasma, and placement positions of empty specimen containers 103c to 103g in which mixed plasma of the respective ratios are prepared are set, so that the test ID is associated with the measurement result. When association is performed at the placement position for the specimen container, the mixed plasma after incubation is placed again at the set placement position during the measurement of the delay type. Alternatively, the placement position for the mixed plasma may be changed during the measurement of the delay type by setting the placement position again during the measurement of the delay type. A method other than the setting of the placement position may be used as long as the test ID can be associated with the measurement result. In addition, examples of the method include a method in which a unique bar code including information such as a mixed plasma ratio of the target test plasma and classification of an immediate type and a delay type is attached to each of the containers containing the mixed plasma and is read by an automatic analysis device, or a method in which a test ID attached to the test plasma is read and a specimen set subsequent thereto is identified as a mixed plasma. The method for preparing the mixed plasma in the present embodiment is the same as the preparation method in Embodiment 1 shown in FIG. 3.

Next, processing of creating a graph in the present embodiment will be described. FIG. 19 is a flowchart showing a method for measuring a prepared specimen and creating a graph. First, when the preparation of the mixed plasma is completed (step S1901), the analysis operation control unit 120a creates a request of the immediate type and the delay type (step S1902), and the operator determines whether to continue the measurement of the immediate type on the screen shown in FIG. 10 (step S1903). The measurement unit measures specimens of respective mixing ratios, and the coagulation time calculation unit 120b calculates the coagulation time of each mixed plasma based on the measurement result (step S1904).

FIG. 20 shows an example of a selection screen of measurement results in Embodiment 3. In the present embodiment, when the operator selects, from a list of the measurement results shown in FIG. 20, a test ID for which a graph is desired to be created, the measurement result associated with the test ID is automatically displayed in the left column, the upper right column, and/or the lower right column. All the measurement results associated with the test ID are displayed in the left column, measurement results related to the immediate type are displayed in the upper right column, and measurement results related to the delay type are displayed in the lower right column. Only the measurement of the immediate type is completed up to step S1904, and therefore, the measurement results of the immediate type are automatically displayed in the left column and the upper right column. When the operator taps a graph creation button to make an instruction of creating a graph (S1905), the graph creation unit 120c creates a graph of the immediate type using the measurement results displayed in the upper right column (S1906), and the graph is displayed on the display unit. The operator checks the graph of the immediate type (step S1907). In Embodiment 1, the measurement results used for creating the graph are manually added to the upper right column and/or the lower right column. In the present embodiment, the specimen measurement result to be subjected to the cross-mixing test is managed by one test ID, and when the test ID is selected, the measurement result associated with the test ID can be automatically selected, and the time and effort of the operator during creation of the graph can be reduced.

When the measurement of the delay type is continuously performed, the operator closes the container containing plasma at each mixing ratio after the measurement of the immediate type, and incubation is performed, for example, at 37° C. for 2 hours (step S1908). In the present embodiment, the mixed plasma for the measurement of the delay type is incubated outside the automatic analysis device 100, and the invention is not limited to the present embodiment. The specimen incubated outside the automatic analysis device 100 is placed on the specimen disk 102 by the operator (step S1909). As described above, when the test ID and the measurement result are associated with each other at the placement position for the specimen container 103 on the mixed plasma adjustment setting screen shown in FIG. 18, the operator places the incubated specimen at the position set on the mixed plasma adjustment setting screen. Here, when it is desired to change the placement position, the position can be changed based on the operation screen.

Thereafter, the operator makes an instruction of the measurement of the delay type using the input unit. In a measurement instruction screen (not shown), the placement position for the specimen container filled with the mixed plasma can be set, and when it is desired to change the placement position for the specimen container during the measurement of the delay type, the operator sets the placement position again in the present step (step S1910), the measurement unit measures the plasma at each mixing ratio, and the coagulation time calculation unit 120b calculates the coagulation time of each mixed plasma based on the measurement result (step S1911). When the operator selects, from the list of the measurement results shown in FIG. 20, the test ID for which a graph is desired to be created, the measurement result associated with the test ID is automatically displayed in the left column, the upper right column, and/or the lower right column. Here, the measurements of the immediate type and the delay type are completed, and therefore, the measurement results of the immediate type and the delay type are displayed in the left column, the measurement result of the immediate type is automatically displayed in the upper right column, and the measurement result of the delay type is automatically displayed in the lower right column. When the operator taps the graph creation button to make an instruction of generating a graph (step 1912), the graph creation unit 120c creates graphs of the immediate type and the delay type based on the coagulation time of each mixed plasma calculated by the coagulation time calculation unit 120b (step S1913). The graphs of the immediate type and the delay type created by the graph creation unit 120c are output to the display unit on one screen, and the operator checks the graph (step S1914).

The case where the test ID and the measurement result are associated with each other by the placement position has been described in detail in the present embodiment, but the invention is not limited to this method. In another method, in a case where a unique bar code including information such as a mixed plasma ratio of the target test plasma and classification of an immediate type and a delay type is attached to each of the containers containing the mixed plasma and is read by a device, or in a case where a test ID attached to the test plasma is read and a specimen set subsequent thereto is identified as a mixed plasma, the device can read the individual identification number and automatically recognize the test ID when the container is placed on any position.

In the present embodiment, the example in which the test ID is associated with the measurement results of the immediate type and the delay type has been described in detail. When performing a measurement of either immediate type or delay type and graph creation, a test ID may be input and the measurement results may be associated with the test ID. In this case, the time and effort for creating a graph can also be reduced.

When the measurement result displayed on the list screen of the measurement results shown in FIG. 20 includes a measurement result with an error, the method for estimating the coagulation time according to Embodiment 1 or Embodiment 2 may be used. Alternatively, the measurement result with an error may be deleted from the list screen, the graph may be created using the measurement results excluding the measurement result with an error, or the graph may be created using the coagulation time calculated for the mixed plasma prepared outside the automatic analysis device 100.

Embodiment 4

In Embodiment 4, it is possible to select whether to continuously measure the mixed plasma from the preparation to the measurement. FIG. 21 is an example of a selection screen according to Embodiment 4. In the screen shown in FIG. 21, before the preparation of the mixed plasma used in the cross-mixing test, the measurement of the prepared specimen, and the creation of the graph, the operator selects one of the following: (1) only preparation of mixed plasma; (2) only measurement (use of manually prepared specimen); and (3) preparation of mixed plasma+measurement. When the item (1) only the preparation of the mixed plasma is selected and executed, the preparation of the mixed plasma is executed as shown in the flowchart of FIG. 3 in Embodiment 1, and the operation is completed without the measurement of the prepared specimen or the creation of a graph. When the item (2) only the measurement (use of manually prepared specimen) is selected and executed, the preparation of mixed plasma is not performed, but the measurement of the prepared specimen and the creation of a graph are executed as shown in the flowchart of FIG. 9 in Embodiment 1 or FIG. 19 in Embodiment 3. By providing the selection screen as shown in FIG. 21, the mixed plasma prepared outside the automatic analysis device 100 can be analyzed.

When the item (3) the preparation of mixed plasma+measurement is selected and executed, the transition is made to the mixed plasma adjustment setting screen shown in FIG.

4 in Embodiment 1 and the mixed plasma adjustment setting screen shown in FIG. 18 in Embodiment 3, and the preparation of mixed plasma is executed as shown in the flowchart of FIG. 3 in Embodiment 1. Thereafter, the measurement of the prepared specimen and the creation of a graph are executed. In the present embodiment, an instruction of an operation performed up to the measurement can be made on the selection screen as shown in FIG. 21 in advance, and therefore, it is possible to omit the immediate type instruction request in step S902 or the delay type instruction request in step S908 in Embodiment 1, and the immediate type measurement instruction in step S1903 or the delay type instruction request in step S1910 in Embodiment 2, and the work of the operator can be reduced. The present embodiment is basically the same as Embodiment 1 in other points, and is also applicable to Embodiment 3. In addition, the method described in Embodiment 2 may also be applied to the method for estimating the coagulation time in the present embodiment.

REFERENCE SIGNS LIST

100: automatic analysis device
101: specimen dispensing mechanism
101a: specimen dispensing probe
102: specimen disk
103: specimen container
104: reaction container
105: specimen syringe pump
106: reagent dispensing mechanism
106a: reagent dispensing probe
107: reagent disk
108: reagent container
109: reagent heating mechanism
110: reagent syringe pump
111: reaction container stock unit
112: reaction container transport mechanism
113: detection unit
114: reaction container placing unit
115: light source
116: light receiving unit
117: reaction container discarding unit
118: input and output unit
118a: mouse
118b: keyboard
118c: display
119: storage unit
120: control unit
120a: analysis operation control unit
120b: coagulation time calculation unit
120c: graph creation unit
121: A/D converter
122: interface
123: printer
124: incubator

The invention claimed is:

1. An automatic analysis device comprising:
a specimen dispensing mechanism configured to dispense test plasma and/or normal plasma added to correct a coagulation time of the test plasma into a plurality of empty specimen containers, and to dispense each of prepared specimens containing only the test plasma, only the normal plasma, or mixed plasma obtained by mixing the test plasma and the normal plasma from the specimen container to a reaction container;
a reagent dispensing mechanism configured to dispense a reagent into the reaction container;

a measurement unit configured to emit light from a light source to the prepared specimen to which the reagent is added in the reaction container and to measure a light intensity of obtained scattered light or transmitted light;
an analysis operation control unit configured to control operations of the specimen dispensing mechanism, the reagent dispensing mechanism, and the measurement unit;
a coagulation time calculation unit configured to calculate a coagulation time based on the light intensity measured by the measurement unit;
a graph creation unit configured to create a graph related to a coagulation time of each prepared specimen calculated by the coagulation time calculation unit; and
a display unit configured to display the graph created by the graph creation unit, wherein
when a prepared specimen for which the coagulation time is incalculable is present, the graph creation unit creates a graph using at least one of a coagulation time calculated by the coagulation time calculation unit for a prepared specimen prepared outside the automatic analysis device, and a coagulation time estimated by the coagulation time calculation unit based on the light intensity measured by the measurement unit.

2. The automatic analysis device according to claim 1, wherein
the display unit makes a display to prompt deletion of the prepared specimen for which the coagulation time is incalculable from a graph creation target by the graph creation unit, and
when the deletion is selected, the graph creation unit creates a graph using only a prepared specimen for which the coagulation time has been calculated.

3. The automatic analysis device according to claim 1, wherein
the coagulation time calculation unit calculates a reference intensity difference that is an intensity difference between a light intensity at a coagulation reaction start level and a light intensity at a coagulation reaction end level, and calculates, as a coagulation time, a time until an intensity difference with the coagulation reaction start level reaches a predetermined ratio with respect to the reference intensity difference, and
when a prepared specimen for which a measurement of a light intensity has been ended before the coagulation reaction end level is reached is present,
the coagulation time calculation unit estimates a coagulation time of the prepared specimen by estimating a reference intensity difference of the prepared specimen using a reference intensity difference of another prepared specimen, and
the graph creation unit creates a graph using each of the estimated coagulation time for the prepared specimen and a calculated coagulation time for the other prepared specimen.

4. The automatic analysis device according to claim 3, wherein
the display unit displays the estimated coagulation time separately from the calculated coagulation time.

5. The automatic analysis device according to claim 3, wherein
the coagulation reaction start level and the coagulation reaction end level are determined based on a second derivative of the light intensity.

6. The automatic analysis device according to claim 3, wherein when the prepared specimen for which the measurement of the light intensity has been ended before the predetermined ratio is reached with respect to the estimated reference intensity difference, the coagulation time calculation unit estimates, as the coagulation time, a time until a first derivative of the light intensity reaches a peak after the coagulation reaction start level, and the graph creation unit creates a graph using the estimated coagulation time for all the prepared specimens.

7. The automatic analysis device according to claim 1, wherein the display unit makes a display to prompt switching to at least one of a percentile method or a first derivative method as a calculation method for the coagulation time by the coagulation time calculation unit, and when the percentile method is selected, the coagulation time calculation unit calculates a reference intensity difference that is an intensity difference between a light intensity at a coagulation reaction start level and a light intensity at a coagulation reaction end level, and calculates, as a coagulation time, a time until an intensity difference with the coagulation reaction start level reaches a predetermined ratio with respect to the reference intensity difference, and when the first derivative method is selected, the coagulation time calculation unit calculates, as a coagulation time, a time until a first derivative of the light intensity reaches a peak after the coagulation reaction start level.

8. The automatic analysis device according to claim 1, wherein the coagulation time calculation unit calculates a reference intensity difference that is an intensity difference between a light intensity at a coagulation reaction start level and a light intensity at a coagulation reaction end level, and calculates, as a coagulation time, a time until an intensity difference with the coagulation reaction start level reaches a predetermined ratio with respect to the reference intensity difference, and when the prepared specimen for which the coagulation time is incalculable is present, the coagulation time calculation unit estimates a coagulation time of the prepared specimen by estimating a coagulation reaction curve using a second derivative of the light intensity measured by the measurement unit, and the graph creation unit creates a graph using each of the estimated coagulation time for the prepared specimen and a calculated coagulation time for another prepared specimen.

9. The automatic analysis device according to claim 8, wherein when the coagulation reaction curve is inestimable, the coagulation time calculation unit estimates, as the coagulation time, a time until a first derivative of the light intensity reaches a peak after the coagulation reaction start level, and the graph creation unit creates a graph using the estimated coagulation time for all the prepared specimens.

10. The automatic analysis device according to claim 1, wherein when the prepared specimen for which the coagulation time is incalculable is present, the graph creation unit creates a graph using the coagulation time estimated by the coagulation time calculation unit.

11. The automatic analysis device according to claim 1, wherein the coagulation time of each prepared specimen used for creating the graph is managed by one test ID.

12. An automatic analysis method using an automatic analysis device including a specimen dispensing mechanism, a reagent dispensing mechanism, a measurement unit, a coagulation time calculation unit, a graph creation unit, and a display unit, the method comprising:

a step of dispensing test plasma and/or normal plasma added to correct a coagulation time of the test plasma into a plurality of empty specimen containers, and dispensing each of prepared specimens containing only the test plasma, only the normal plasma, or mixed plasma obtained by mixing the test plasma and the normal plasma from the specimen container to a reaction container, by the specimen dispensing mechanism;

a step of dispensing a reagent into the reaction container by the reagent dispensing mechanism;

a step of emitting light from a light source to the prepared specimen to which the reagent is added in the reaction container and measuring a light intensity of obtained scattered light or transmitted light, by the measurement unit;

a step of calculating, by the coagulation time calculation unit, a coagulation time based on the light intensity measured by the measurement unit;

a step of creating, by the graph creation unit, a graph related to a coagulation time of each prepared specimen calculated by the coagulation time calculation unit;

a step of displaying, by the display unit, the graph created by the graph creation unit; and a step of creating, by the graph creation unit, a graph using at least one of a coagulation time calculated for a prepared specimen prepared outside the automatic analysis device and a coagulation time estimated by the coagulation time calculation unit based on a light intensity measured using another prepared specimen, when a prepared specimen for which the coagulation time is incalculable is present.

13. The automatic analysis method according to claim 12, further comprising:

a step of making, by the display unit, a display to prompt deletion of the prepared specimen for which the coagulation time is incalculable from a graph creation target by the graph creation unit; and a step of creating, by the graph creation unit, a graph using only a prepared specimen for which the coagulation time has been calculated, when the deletion is selected.

14. The automatic analysis method according to claim 12, wherein the coagulation time calculation unit calculates a reference intensity difference that is an intensity difference between a light intensity at a coagulation reaction start level and a light intensity at a coagulation reaction end level, and calculate, as a coagulation time, a time until an intensity difference with the coagulation reaction start level reaches a predetermined ratio with respect to the reference intensity difference, and the automatic analysis method further includes:

when a prepared specimen for which a measurement of a light intensity has been ended before the coagulation reaction end level is reached is present, a step of estimating, by the coagulation time calculation unit, a coagulation time of the prepared specimen by estimating a reference intensity difference of the prepared specimen using a reference intensity difference of another prepared specimen; and a step of creating, by the graph creation unit, a graph using each of the estimated coagulation time for the prepared specimen and a calculated coagulation time for the other prepared specimen.

15. The automatic analysis method according to claim 12, further comprising:

a step of making, by the display unit, a display to prompt switching to at least one of a percentile method or a first derivative method as a calculation method for the coagulation time by the coagulation time calculation unit;

a step of calculating a reference intensity difference that is an intensity difference between a light intensity at a coagulation reaction start level and a light intensity at a coagulation reaction end level, and calculating, as a coagulation time, a time until an intensity difference with the coagulation reaction start level reaches a predetermined ratio with respect to the reference intensity difference by the coagulation time calculation unit when the percentile method is selected; and a step of calculating, as a coagulation time, by the coagulation time calculation unit, a time until a first derivative of the light intensity reaches a peak after the coagulation reaction start level when the first derivative method is selected.

16. The automatic analysis method according to claim 12, wherein the coagulation time calculation unit calculates a reference intensity difference that is an intensity difference between a light intensity at a coagulation reaction start level and a light intensity at a coagulation reaction end level, and calculates, as a coagulation time, a time until an intensity difference with the coagulation reaction start level reaches a predetermined ratio with respect to the reference intensity difference, and the automatic analysis method further includes:

when the prepared specimen for which the coagulation time is incalculable is present, a step of estimating, by the coagulation time calculation unit, a coagulation time of the prepared specimen by estimating a coagulation reaction curve using a second derivative of the light intensity measured by the measurement unit; and a step of creating, by the graph creation unit, a graph using each of the estimated coagulation time for the prepared specimen and a calculated coagulation time for the other prepared specimen.

17. The automatic analysis method according to claim 12, wherein the coagulation time of each prepared specimen used for creating the graph is managed by one test ID.

* * * * *